United States Patent
Reynolds

(10) Patent No.: US 8,574,244 B2
(45) Date of Patent: Nov. 5, 2013

(54) SYSTEM FOR CLOSING A PUNCTURE IN A VESSEL WALL

(75) Inventor: Timothy C. Reynolds, Sunnyvale, CA (US)

(73) Assignee: Abbott Laboratories, Abbott Park, IL (US)

( * ) Notice: Subject to any disclaimer, the term of this patent is extended or adjusted under 35 U.S.C. 154(b) by 1292 days.

(21) Appl. No.: 11/960,593

(22) Filed: Dec. 19, 2007

(65) Prior Publication Data

US 2008/0319458 A1 Dec. 25, 2008

Related U.S. Application Data

(60) Provisional application No. 60/946,063, filed on Jun. 25, 2007.

(51) Int. Cl.
*A61B 17/04* (2006.01)
*A61B 17/12* (2006.01)

(52) U.S. Cl.
USPC ............................................. 606/144

(58) Field of Classification Search
USPC ........................................ 606/139, 144–150
See application file for complete search history.

(56) References Cited

U.S. PATENT DOCUMENTS

| | | |
|---|---|---|
| 312,408 A | 2/1885 | Wackerhagen |
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,108,206 A | 2/1938 | Meeker |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

U.S. Appl. No. 60/506,536, filed Sep. 26, 2003, McIntosh.

(Continued)

*Primary Examiner* — Melanie Tyson
(74) *Attorney, Agent, or Firm* — Workman Nydegger; Randy Shen

(57) ABSTRACT

A device is provided herein for deploying a suture in a puncture through a vessel wall of a blood vessel, the puncture disposed within a tissue tract of a patient body. The device includes a shaft suitable for insertion along the tissue tract and into the vessel through a puncture, a plurality of needles, each needle having a proximal end and a distal end suitable for forming a needle path through the vessel wall, wires associated with each needle, each wire having a distal end and a proximal end, and hooks coupled to each of the distal ends of each wire, each hook being configured to anchor the wire to an interior portion of the vessel wall.

18 Claims, 15 Drawing Sheets

(56) References Cited

U.S. PATENT DOCUMENTS

| | | |
|---|---|---|
| 2,610,631 A | 9/1952 | Calicchio |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,814,104 A | 6/1974 | Irnich et al. |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,011,872 A | 3/1977 | Komiya |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,501,276 A | 2/1985 | Lombardi |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,830,002 A | 5/1989 | Semm |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,287 A | 3/1993 | Fournier et al. |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,471 A | 6/1993 | Burkhart |
| 5,217,485 A | 6/1993 | Liu et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,237,996 A | 8/1993 | Waldman et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bagnato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |

(56) References Cited

U.S. PATENT DOCUMENTS

| | | |
|---|---|---|
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,279 A | 10/1994 | Hofling |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,330 A | 4/1995 | Tuason |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A * | 5/1995 | Jackson et al. .................. 606/1 |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,478,354 A | 12/1995 | Tovey et al. |
| 5,480,407 A | 1/1996 | Wan et al. |
| 5,486,190 A | 1/1996 | Green |
| 5,489,295 A | 2/1996 | Piplani et al. |
| 5,492,119 A | 2/1996 | Abrams |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,267 A | 7/1996 | Edwards et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,647,372 A | 7/1997 | Tovey et al. |
| 5,649,959 A | 7/1997 | Hannam et al. |
| 5,662,664 A | 9/1997 | Gordon et al. |
| 5,669,917 A | 9/1997 | Sauer et al. |
| 5,672,174 A | 9/1997 | Gough et al. |
| 5,674,231 A | 10/1997 | Green et al. |
| 5,676,689 A | 10/1997 | Kensey et al. |
| 5,693,061 A | 12/1997 | Pierce et al. |
| 5,700,273 A | 12/1997 | Buelna et al. |
| 5,707,379 A | 1/1998 | Fleenor et al. |
| 5,713,899 A | 2/1998 | Marnay et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,143 A | 3/1998 | Gough et al. |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,759,189 A | 6/1998 | Ferragamo et al. |
| 5,766,183 A | 6/1998 | Sauer |
| 5,766,186 A | 6/1998 | Faraz et al. |
| 5,766,217 A | 6/1998 | Christy |

(56) References Cited

U.S. PATENT DOCUMENTS

| | | | |
|---|---|---|---|
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,576 A | 1/1999 | LeVeen et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,897,487 A | 4/1999 | Ouchi |
| 5,897,564 A | 4/1999 | Schulze et al. |
| 5,902,311 A | 5/1999 | Andreas et al. |
| 5,904,697 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,547 A | 9/1999 | Gough et al. |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,517 A | 11/1999 | Gough et al. |
| 5,980,539 A | 11/1999 | Kontos |
| 5,993,466 A | 11/1999 | Yoon |
| 5,993,476 A | 11/1999 | Groiso |
| 5,997,555 A | 12/1999 | Kontos |
| 6,001,109 A | 12/1999 | Kontos |
| 6,009,877 A | 1/2000 | Edwards |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,056,744 A | 5/2000 | Edwards |
| 6,068,603 A | 5/2000 | Suzuki |
| 6,077,276 A | 6/2000 | Kontos |
| 6,077,279 A | 6/2000 | Kontos |
| 6,083,242 A | 7/2000 | Cook |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A * | 10/2000 | Modesitt et al. ............... 606/144 |
| 6,139,556 A | 10/2000 | Kontos |
| 6,143,004 A | 11/2000 | Davis |
| 6,152,936 A | 11/2000 | Christy et al. |
| 6,165,183 A * | 12/2000 | Kuehn et al. ................... 606/139 |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 * | 3/2001 | Levinson ....................... 606/144 |
| 6,221,084 B1 | 4/2001 | Fleenor |
| 6,245,079 B1 | 6/2001 | Nobles et al. |
| 6,248,124 B1 | 6/2001 | Pedros et al. |
| 6,296,657 B1 | 10/2001 | Brucker |
| 6,306,081 B1 | 10/2001 | Ishikawa et al. |
| 6,322,580 B1 | 11/2001 | Kanner |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,397,110 B1 | 5/2002 | Kuzma |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,461,366 B1 | 10/2002 | Seguin |
| 6,511,489 B2 | 1/2003 | Field et al. |
| 6,517,498 B1 | 2/2003 | Burbank et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,159 B1 | 5/2003 | Edwards et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,689,051 B2 | 2/2004 | Nakada et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,776,785 B1 | 8/2004 | Yencho et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 * | 6/2005 | Nobles et al. ................. 606/144 |
| 6,939,357 B2 | 9/2005 | Navarro et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,060,084 B1 | 6/2006 | Loshakove et al. |
| 7,063,661 B2 | 6/2006 | Okada |
| 7,063,710 B2 | 6/2006 | Takamoto et al. |
| 7,063,711 B1 | 6/2006 | Loshakove et al. |
| 7,083,635 B2 | 8/2006 | Ginn |
| 7,108,710 B2 | 9/2006 | Anderson |
| 7,112,225 B2 | 9/2006 | Ginn |
| 7,122,002 B2 | 10/2006 | Okada |
| 7,147,646 B2 | 12/2006 | Dana et al. |
| 7,160,309 B2 | 1/2007 | Voss |
| 7,179,266 B2 | 2/2007 | Kontos |
| 7,229,458 B2 | 6/2007 | Boecker et al. |

(56) References Cited

U.S. PATENT DOCUMENTS

| | | |
|---|---|---|
| 7,235,087 B2 | 6/2007 | Modesitt et al. |
| 7,270,672 B1 | 9/2007 | Singer |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,431,727 B2 | 10/2008 | Cole et al. |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,507,200 B2 | 3/2009 | Okada |
| 7,727,249 B2 | 6/2010 | Rahmani |
| 7,731,655 B2 | 6/2010 | Smith et al. |
| 7,749,249 B2 | 7/2010 | Gelbart et al. |
| 7,753,923 B2 | 7/2010 | St. Goar et al. |
| 7,837,696 B2 | 11/2010 | Modesitt et al. |
| 8,211,122 B2 | 7/2012 | McIntosh |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2002/0188275 A1 | 12/2002 | McGuckin |
| 2003/0093093 A1 | 5/2003 | Modesitt et al. |
| 2003/0195529 A1 | 10/2003 | Takamoto et al. |
| 2003/0233095 A1 | 12/2003 | Urbanski et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0143761 A1 | 6/2005 | Modesitt et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0079914 A1 | 4/2006 | Modesitt et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0142785 A1 | 6/2006 | Modesitt et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2007/0032798 A1 | 2/2007 | Pantages et al. |
| 2007/0032799 A1 | 2/2007 | Pantages et al. |
| 2007/0032801 A1 | 2/2007 | Pantages et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0112304 A1 | 5/2007 | Voss |
| 2007/0123817 A1 | 5/2007 | Khosravi et al. |
| 2007/0167959 A1 | 7/2007 | Modesitt et al. |
| 2007/0203506 A1 | 8/2007 | Sibbitt, Jr. et al. |
| 2007/0276410 A1 | 11/2007 | McIntosh |
| 2007/0282354 A1 | 12/2007 | McIntosh |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0088779 A1 | 4/2009 | Zung et al. |
| 2009/0157105 A1 | 6/2009 | Zung et al. |
| 2009/0254119 A1 | 10/2009 | Sibbitt, Jr. et al. |
| 2010/0130965 A1 | 5/2010 | Sibbitt, Jr. et al. |
| 2012/0053600 A1 | 3/2012 | Fortson |
| 2012/0150201 A1 | 6/2012 | Pantages et al. |
| 2012/0316579 A1 | 12/2012 | Ma |
| 2013/0006277 A1 | 1/2013 | Stafford |
| 2013/0012962 A1 | 1/2013 | Stone |
| 2013/0066340 A1 | 3/2013 | Pantages et al. |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 543 499 | 10/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |

(56) References Cited

FOREIGN PATENT DOCUMENTS

| | | |
|---|---|---|
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/99134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/25014 | 3/2007 |
| WO | WO 2007/25017 | 3/2007 |
| WO | WO 2007/25018 | 3/2007 |
| WO | WO 2007/25019 | 3/2007 |
| WO | WO 2007/81836 | 7/2007 |
| WO | WO 2010/031050 | 3/2010 |

OTHER PUBLICATIONS

U.S. Appl. No. 60/540,811, filed Jan. 30, 2004, McIntosh.
U.S. Appl. No. 60/711,279, filed Aug. 24, 2005, Sibbitt, Jr. et al.
U.S. Appl. No. 60/726,985, filed Oct. 14, 2005, Sibbitt Jr. et al.
U.S. Appl. No. 60/946,063, filed Jun. 25, 2007, Reynolds.
U.S. Appl. No. 61/097,072, filed Sep. 15, 2008, Sibbitt Jr. et al.
U.S. Appl. No. 90/006,469, filed Nov. 29, 2002, Modesitt, et al.
US 5,820,544, Jun. 1, 1974, Semm (withdrawn).
Cardiac Catheterization and Angiography, 3rd Ed., Lea N. ad Febiger, Philadelphia, 1986. Elgiloy Brochure, Jun. 23, 1959, Elgin National Watch Co., Elgin, IL.
Cardio-Thoracic Systems Prospectus dated Mar. 20, 1996.
Datascope Corporation, Montvale, NJ (1991) 1 PG, American Heart Assoc. Meeting, Anaheim.
Elgiloy Brochure, Jun. 23, 1959, Elgin National Watch Co., Elgin, IL.
Marshall, A.C. & Lock, J.E.; "Structural and compliant anatomy of the patent foramen ovale in patients undergoing transcatheter closure", Am. Heart Journ., 140(2):303-307 (2000).
Nakamura, S. et al., Techniques for Palmaz-Schatz Stent Deployment in Lesions With A Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Serruys, PW et al., A Comparision of Balloon-Expandable-Stent Implantaion With Balloon Angioplasty in Patients With Coronary Artery Disease, New England Journal of Medicine, 331:489-495, 1994.

Taber's Cyclopedic Medical Dictionary, 18th Ed., p. 747 (1997).
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/729,541, Dec. 12, 2006, Office Action.

(56) References Cited

OTHER PUBLICATIONS

U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/877,974, Jul. 9, 2008, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/948,445, Jul. 11, 2007, Office Action.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/273,107, Jun. 2, 2010, Office Action.
U.S. Appl. No. 11/316,775, Apr. 16, 2008, Office Action.
U.S. Appl. No. 11/316,775, Aug. 6, 2008, Office Action.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,513, Apr. 9, 2010, Office Action.
U.S. Appl. No. 11/891,513, Sep. 28, 2010, Office Action.
U.S. Appl. No. 12/257,127, Aug. 30, 2010, Office Action.
U.S. Appl. No. 12/365,397, Sep. 13, 2010, Office Action.
U.S. Appl. No. 90/006,469, Nov. 29, 2002, Request for Re-Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Re-examination certification.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Rema-Medizintcchnik GmbH, Product Brochure entitled "REMA," Apr. 2001, 7 pages.
Taber's Cyclopedic Medical Dictionary, 18th Ed., p. 747, Feb. 1997.
U.S. Appl. No. 10/948,445, filed Sep. 22, 2004, McIntosh.
U.S. Appl. No. 12/961,239, filed Dec. 6, 2010, Modesitt, et al.
U.S. Appl. No. 12/966,961, filed Dec. 13, 2010, Modesitt, et al.
U.S. Appl. No. 10/909,531, Nov. 23, 2010, Issue Notification.
U.S. Appl. No. 11/363,005, Nov. 10, 2010, Issue Notification.
U.S. Appl. No. 11/465,527, Nov. 10, 2010, Issue Notification.
U.S. Appl. No. 11/552,593, Jul. 22, 2010, Notice of Allowance.
U.S. Appl. No. 11/552,593, Nov. 10, 2010, Issue Notification.
U.S. Appl. No. 11/688,722, Nov. 17, 2010, Issue Notification.
U.S. Appl. No. 12/182,836, Oct. 5, 2010, Office Action.
U.S. Appl. No. 12/257,127, Dec. 22, 2010, Office Action.
U.S. Appl. No. 12/334,085, Dec. 23, 2010, Office Action.
U.S. Appl. No. 12/950,338, filed Nov. 19, 2010, Modesitt, et al.
U.S. Appl. No. 12/955,848, filed Nov. 29, 2010, Modesitt, et al.
U.S. Appl. No. 12/955,863, filed Nov. 29, 2010, Dawn Ma.
U.S. Appl. No. 12/955,869, filed Nov. 29, 2010, Voss.
Kensey Nash Corporation, Exton, PA, "The Hemostatic Puncture Closure Device", retrieved Oct. 23, 2007, 2 pages.
U.S. Appl. No. 11/199,515, Jan. 19, 2011, Issue Notification.
U.S. Appl. No. 10/660,288, Mar. 29, 2011, Office Action.
U.S. Appl. No. 13/022,050, filed Feb. 7, 2011, Pantages et al.
U.S. Appl. No. 09/262,402, Mar. 29, 2000, Office Action.
U.S. Appl. No. 09/262,402, May 30, 2000, Notice of Allowance.
U.S. Appl. No. 11/508,715, Oct. 18, 2010, filed, Office Action.
U.S. Appl. No. 11/891,358, Oct. 19, 2010, Office Action.
U.S. Appl. No. 10/729,541, Nov. 23, 2010, Issue Notification.
U.S. Appl. No. 11/273,107, Oct. 27, 2010, Office Action.
U.S. Appl. No. 11/508,662, Oct. 26, 2010, Office Action.
U.S. Appl. No. 12/334,077, Oct. 27, 2010, Office Action.
U.S. Appl. No. 12/334,085, Jan. 9, 2012, Notice of Allowance.
U.S. Appl. No. 12/955,863, Jan. 6, 2012, Office Action.
U.S. Appl. No. 12/257,127, Jan. 9, 2013, Issue Notification.
U.S. Appl. No. 13/593,154, Jan. 8, 2013, Notice of Allowance.

(56) References Cited

OTHER PUBLICATIONS

U.S. Appl. No. 12/257,127, Jan. 12, 2012, Office Action.
U.S. Appl. No. 12/334,077, Jan. 16, 2013, Office Action.
U.S. Appl. No. 13/615,530, Jan. 17, 2013, Office Action.
U.S. Appl. No. 10/660,288, Feb. 29, 2012, Issue Notification.
U.S. Appl. No. 11/997,379, Feb. 28, 2012, Office Action.
U.S. Appl. No. 12/247,012, Mar. 27, 2013, Issue Notification.
U.S. Appl. No. 13/752,095, filed Jan. 28, 2013, McIntosh.
U.S. Appl. No. 12/247,012, Mar. 16, 2012, Office Action.
U.S. Appl. No. 12/955,869, Mar. 22, 2012, Notice of Allowance.
U.S. Appl. No. 13/593,154, Apr. 10, 2013, Issue Notification.
U.S. Appl. No. 11/891,358, Apr. 10, 2012, Notice of Allowance.
U.S. Appl. No. 12/334,085, Apr. 18, 2012, Issue Notification.
U.S. Appl. No. 13/022,050, Apr. 26, 2012, Office Action.
U.S. Appl. No. 13/870,628, filed Apr. 25, 2013, Ma.
U.S. Appl. No. 12/873,728, May 3, 2013, Office Action.
U.S. Appl. No. 12/182,836, May 17, 2013, Office Action.
U.S. Appl. No. 11/891,513, May 8, 2012, Notice of Allowance.
U.S. Appl. No. 11/997,379, May 11, 2012, Notice of Allowance.
U.S. Appl. No. 12/955,863, May 15, 2012, Notice of Allowance.
U.S. Appl. No. 12/955,869, May 30, 2012, Issue Notification.
U.S. Appl. No. 13/615,530, Jun. 12, 2013, Notice of Allowance.
U.S. Appl. No. 11/199,496, Apr. 28, 2011, Office Action.
U.S. Appl. No. 11/273,107, Jun. 2, 2011, Notice of Allowance.
U.S. Appl. No. 11/997,379, Jul. 13, 2011, Office Action.
U.S. Appl. No. 12/182,836, Jun. 23, 2011, Office Action.
U.S. Appl. No. 12/257,127, Jul. 6, 2011, Office Action.
U.S. Appl. No. 12/950,338, Jun. 15, 2011, Office Action.
U.S. Appl. No. 12/955,848, Jun. 30, 2011, Office Action.
U.S. Appl. No. 13/022,050, Jul. 11, 2011, Office Action.
U.S. Appl. No. 12/334,077, Jul. 21, 2011, Office Action.
U.S. Appl. No. 13/022,050, Jul. 6, 2012, Notice of Allowance.
U.S. Appl. No. 13/525,875, filed Jun. 18, 2012, Voss.
U.S. Appl. No. 12/961,239, Jul. 26, 2011, Notice of Allowance.
U.S. Appl. No. 12/334,085, Aug. 4, 2011, Office Action.
U.S. Appl. No. 12/247,012, Aug. 13, 2012, Notice of Allowance.
U.S. Appl. No. 12/950,338, Aug. 8, 2012, Notice of Allowance.
U.S. Appl. No. 12/955,863, Aug. 8, 2012, Issue Notification.
U.S. Appl. 11/199,496, Aug. 18, 2011, Notice of Allowance.
U.S. Appl. No. 12/966,961, Aug. 18, 2011, Notice of Allowance.
U.S. Appl. No. 11/891,513, Aug. 15, 2012, Issue Notification.
U.S. Appl. No. 11/891,358, Aug. 31, 2011, Notice of Allowance.
U.S. Appl. No. 11/891,513, Aug. 31, 2011, Notice of Allowance.
U.S. Appl. No. 11/997,379, Aug. 29, 2012, Issue Notification.
U.S. Appl. No. 10/660,288, Sep. 30, 2011, Notice of Allowance.
U.S. Appl. No. 11/273,107, Sep. 28, 2011, Issue Notification.
U.S. Appl. No. 12/961,139, Oct. 12, 2011, Issue Notification.
U.S. Appl. No. 12/247,012, Oct. 13, 2011, Office Action.
U.S. Appl. No. 12/955,869, Oct. 18, 2011, Office Action.
U.S. Appl. No. 13/443,659, filed Apr. 10, 2012, Fortson et al.
U.S. Appl. No. 13/445,053, filed Apr. 24, 2012, Fortson et al.
U.S. Appl. No. 12/257,127, Sep. 20, 2012, Notice of Allowance.
U.S. Appl. No. 12/873,728, Sep. 11, 2012, Office Action.
U.S. Appl. No. 12/966,961, Oct. 26, 2011, Issue Notification.
U.S. Appl. No. 11/891,513, Nov. 1, 2011, Notice of Allowance.
U.S. Appl. No. 12/950,338, Nov. 1, 2011, Notice of Allowance.
U.S. Appl. No. 11/891,358, Nov. 18, 2011, Notice of Allowance.
U.S. Appl. No. 12/955,848, Nov. 15, 2011, Office Action.
U.S. Appl. No. 12/950,338, Nov. 14, 2012, Issue Notification.
U.S. Appl. No. 13/022,050, Oct. 31, 2012, Issue Notification.

\* cited by examiner

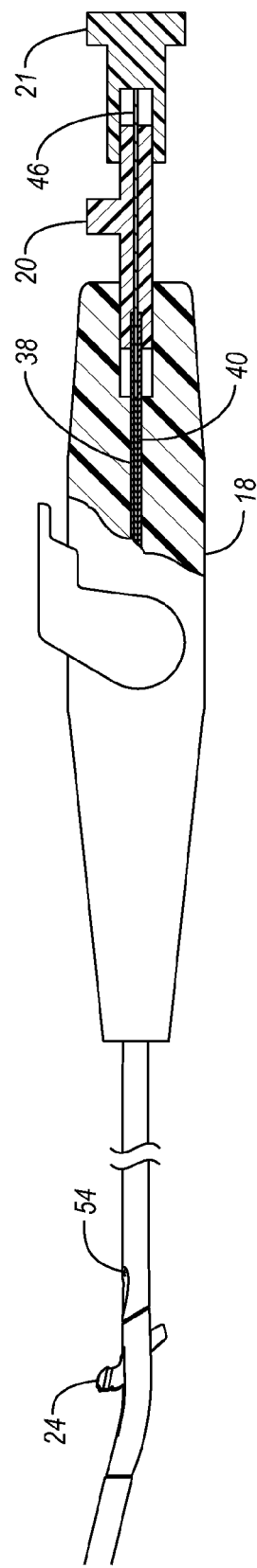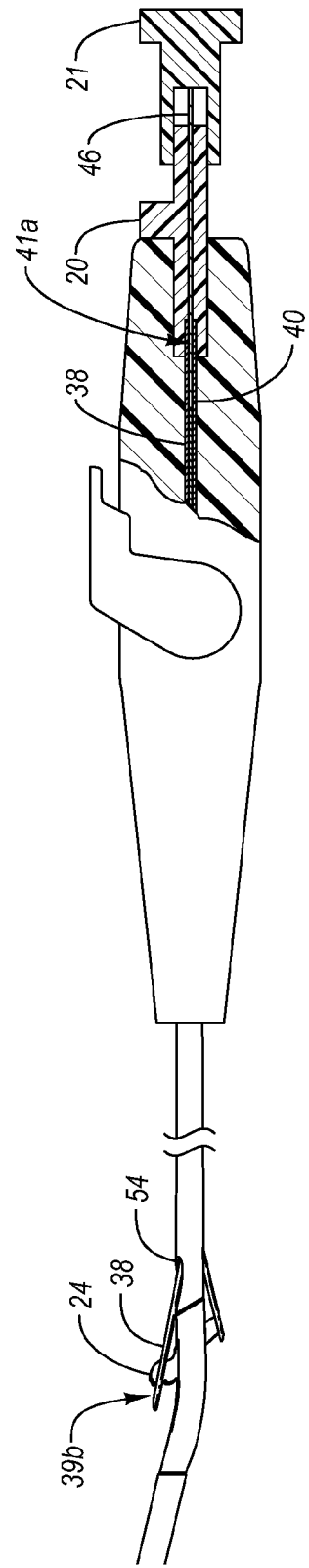

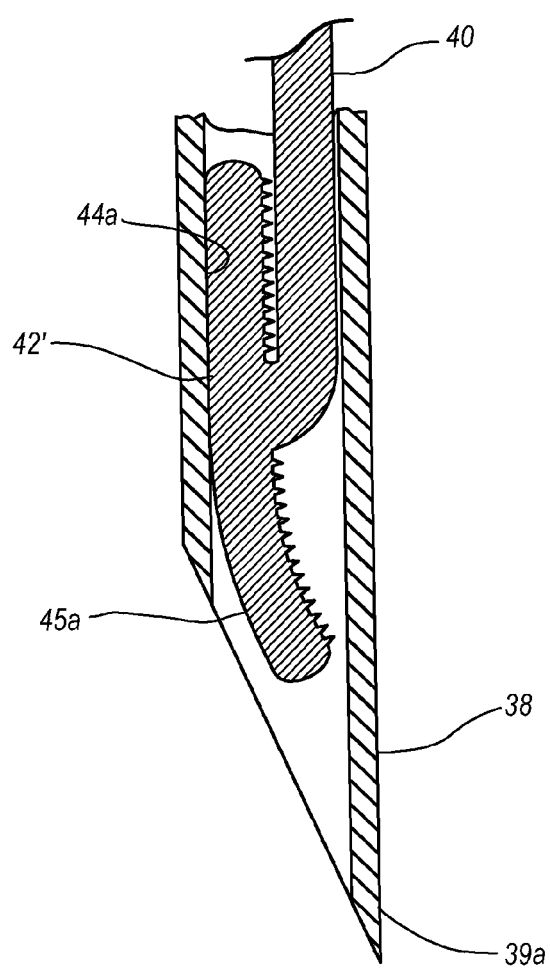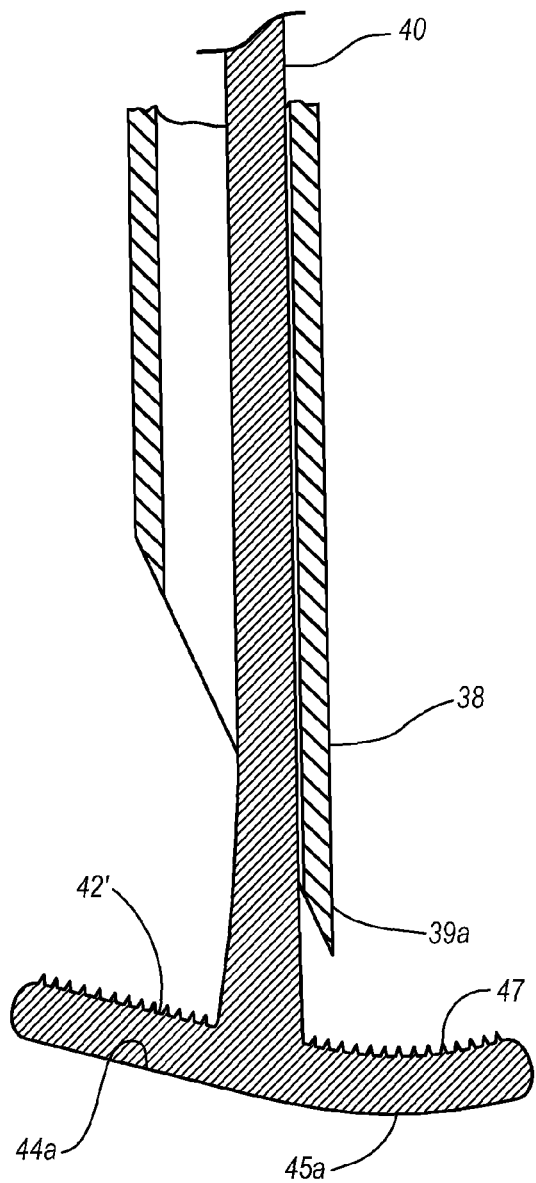
Fig. 23
Fig. 24

SYSTEM FOR CLOSING A PUNCTURE IN A VESSEL WALL

CROSS-REFERENCE TO RELATED APPLICATIONS

This application claims the benefit of U.S. Provisional Patent Application Ser. No. 60/946,063, entitled "System for Closing a Puncture in a Vessel Wall", and filed Jun. 25, 2007, the disclosure of which is incorporated herein by this reference in its entirety.

BACKGROUND

1. Field of the Invention

The present invention relates generally to apparatus and methods for the suturing of body lumens. More particularly, the present invention relates to techniques for percutaneous closure of arterial and venous puncture sites, which are usually accessed through a tissue tract.

2. Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's Cardiac Catheterization and Angioplasty, 3$^{rd}$ Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed, and bleeding at the puncture site is stopped. One common approach for providing hemostasis (the cessation of bleeding) is to apply external force near and upstream from the puncture site, typically by manual or digital compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression induced hemostasis increases when the size of the introducer sheath grows larger, and/or when the patient is anti-coagulated. It is clear that the compression technique for arterial closure can be risky and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the artificial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974, and PCT published Patent Application No. PCT/US96/10271 filed on Jun. 12, 1996, the full disclosures of which are incorporated herein by reference. A suture applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is beneficial to properly direct the needles through the blood vessel wall at a significant distance from the puncture so that the suture is well anchored in the tissue and can provide tight closure. It is also beneficial to ensure that the needle deployment takes place when the device is properly positioned relative to the vessel wall. The ease of deployment and efficacy of the procedure can further be enhanced by reducing the cross-section of that portion of the device which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. It would be particularly beneficial if these improved devices provided some or all of the benefits while overcoming one or more of the disadvantages discussed above.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

A device is provided herein for deploying a suture in a puncture through a vessel wall of a blood vessel, the puncture disposed within a tissue tract of a patient body. The device can include a shaft suitable for insertion along the tissue tract and into the vessel through a puncture; a plurality of needles, each needle includes a proximal end and a distal end suitable for forming a needle path through the vessel wall; wires associated with each needle, each wire includes a distal end and a proximal end; and hooks coupled to each of the distal ends of each wire, each hook being configured to anchor the wire to an interior portion of the vessel wall.

According to one example, a closure device can also be included that includes a body and guide lumens extending beyond the lumens that are in communication with the body. The body can have a clamping or securing mechanism coupled thereto that allows wires to be secured to the body. According to one example, the wires can be fed through the distal ends of the guide lumens to the body and secured thereto by the clamping mechanism. The closure device can be rotated to twist the suture wires and thereby close the puncture. The clamping mechanism may be configured to provide substantially constant tensioning force on the suture wires as the suture wires are twisted. Further, the clamping mechanism may be configured to separately and independently apply tensioning force to each wire. The force may be independently chosen to help ensure that the wires twist equally. In one example, the forces can be approximately equal. The closure device may also include a guide tip coupled to the distal ends of the guide lumens. The guide tip helps ensure that twisting of the wires begins at a desired location away from the vessel wall.

In addition, a method is disclosed herein that can include advancing a plurality of needles through the vessel wall outside the puncture; advancing hooks from a plurality of distal ends of the plurality of needles, wherein the plurality of hooks are coupled to wires and at least a portion of the wires remain outside the vessel wall; anchoring the hooks to interior portions of the vessel wall; and twisting the wires to close the puncture.

Further, a system is disclosed herein that can include a deployment device for positioning hooks within a vessel wall and securing the hooks to an interior portion of the vessel wall. The system may also include a closure device that allows a practitioner to twist the wires to thereby close the vessel wall with the wires.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments of the invention and are not therefore to be considered as limiting of its scope, embodiments will be described and explained with additional specificity and detail through the use of the accompanying drawings in which:

FIGS. 5-7 illustrate deployment of needles according to one example;

FIG. 23-24 are partial cutaway views illustrating another structure associated with a needle.

DETAILED DESCRIPTION

A closure system is provided herein that includes a deployment device and a closure device. According to one example, the deployment device provides for repeatable and reliable deployment of wires within a vessel having a puncture therein. The wires have securing member, such as hooks, on the distal ends thereof that allow the distal ends of the wires to be anchored to a proximal wall of the vessel to be closed. As used herein, a hook shall be broadly understood to mean any structure configured to secure the wires to tissue, such as to secure a wire from moving proximally from engagement with the tissue. According to one example, the wires are deployed by advancing needles from outside the vessel to a location within the vessel. The needles carry the hooks. In particular, the hooks may be stored completely within the needles prior to deployment. A practitioner deploys the hooks by advancing the hooks beyond the distal ends of the needles. Thereafter, the hooks may be anchored to the vessel wall by drawing the wires proximally to draw the hooks into contact with the vessel wall.

The closure device may then be used to twist the wires, which are anchored in the vessel wall, to thereby close the puncture. The closure device may include features for providing tensioning force to the wires during twisting. These forces may be independently applied and/or selected for each wire. Independently applying a constant force to each wire during twisting may help ensure the wire remains anchored while reducing the possibility that the hook will pull through. In addition, independently applied, constant forces may increase the likelihood that the wires will twist uniformly relative to each other, which may help provide uniform and repeatable procedures. Additionally, the closure device may provide a reliable initiation location for the twist that is away from the vessel wall. By initiating the twist at a location away from the vessel wall, the closure device may reduce distortion of the vessel wall during twisting. Further, the closure device may include a wire-loading device to facilitate loading of the wires into the closure device.

Figure 1:
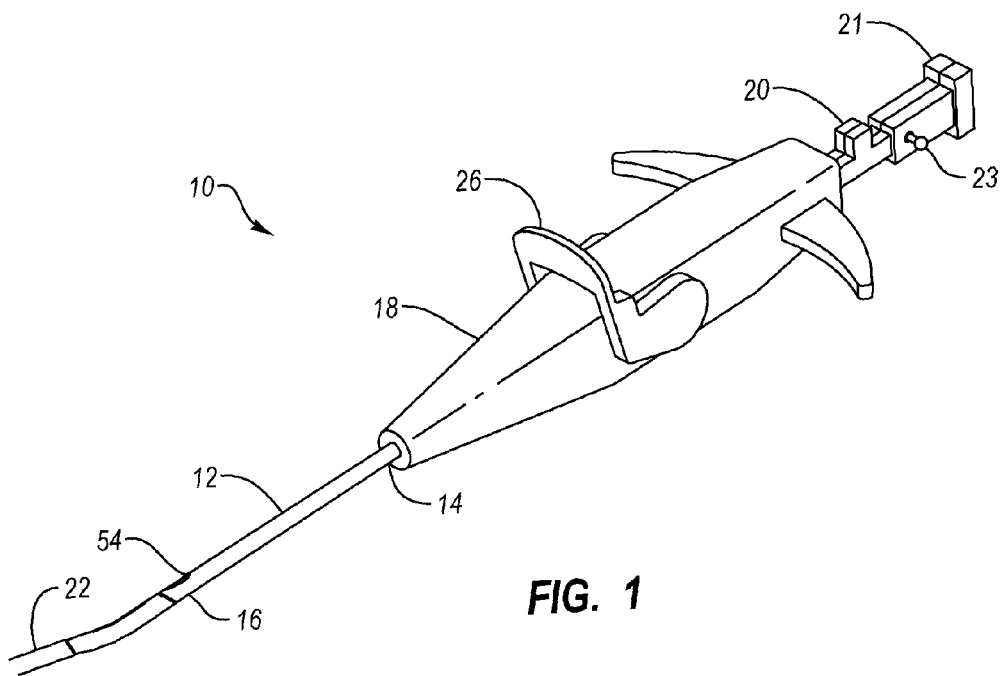
FIG. 1 is a perspective view of a deployment device according to one example.

Referring now to FIG. 1, a deployment device 10 can generally have a shaft 12 having a proximal end 14 and a distal end 16. A proximal housing 18 supports a needle deployment handle 20 as well as a hook deployment handle 21. A flexible, atraumatic monorail guidebody 22 extends distally of the distal end 16 of the shaft 12.

Figure 2:
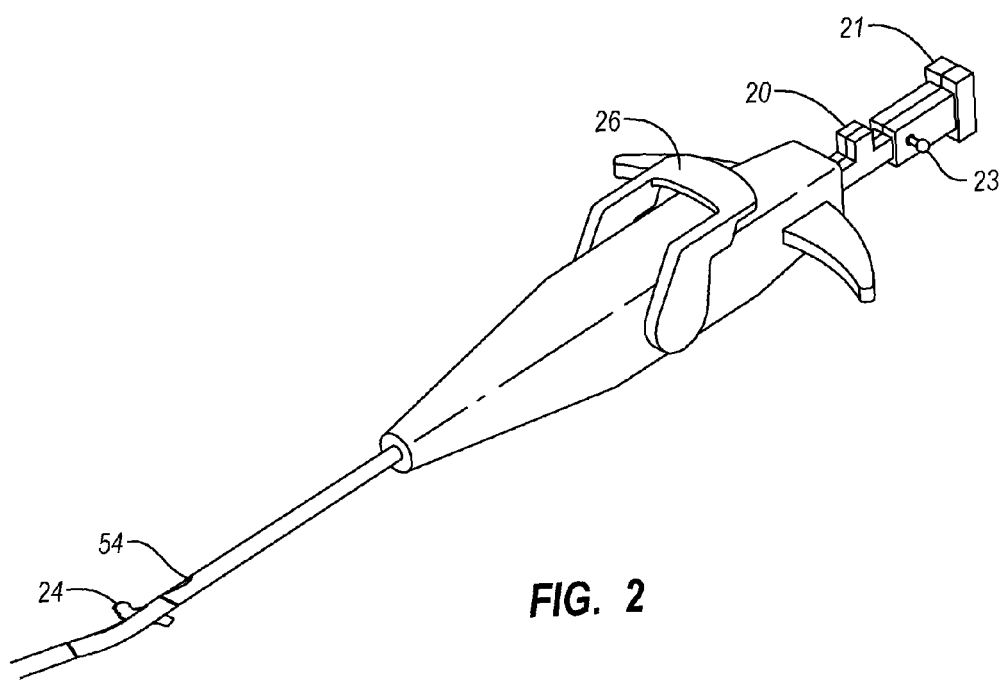
FIG. 2 illustrates the deployment device of FIG. 1 in which an elongate foot is shown in a deployed position.

As can be seen with reference to FIG. 2, a foot 24 is articulatably mounted near the distal end 16 of the shaft 12. The foot 24 moves between a low profile configuration, in which the foot 24 is substantially aligned along an axis of shaft 12 (as illustrated in FIG. 1), to a deployed position, in which the foot 24 extends laterally from the shaft 12, upon actuation of a foot deployment handle 26 disposed on the proximal housing 18.

FIGS. 1 and 2 also illustrate the structure and deployment of the foot 24. In particular, actuation of the foot deployment handle 26 occurs by rotating the foot deployment handle 26 from the position shown in FIG. 1 to the position shown in FIG. 2. As the foot deployment handle 26 is thus rotated, the foot 24 is moved from the parked position shown in FIG. 1 to the deployed position shown in FIG. 2.

Figure 3:
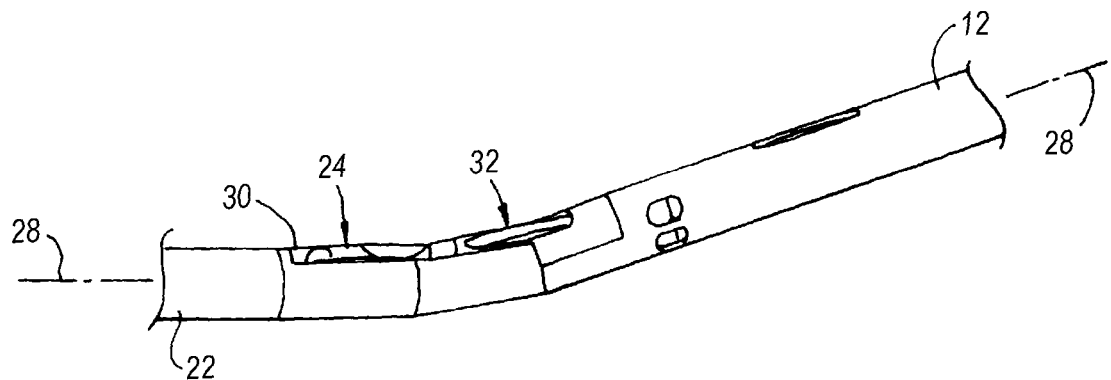
FIG. 3 illustrates the deployment device of FIG. 1 in which an elongate foot is shown in an undeployed position in more detail.
Figure 4:
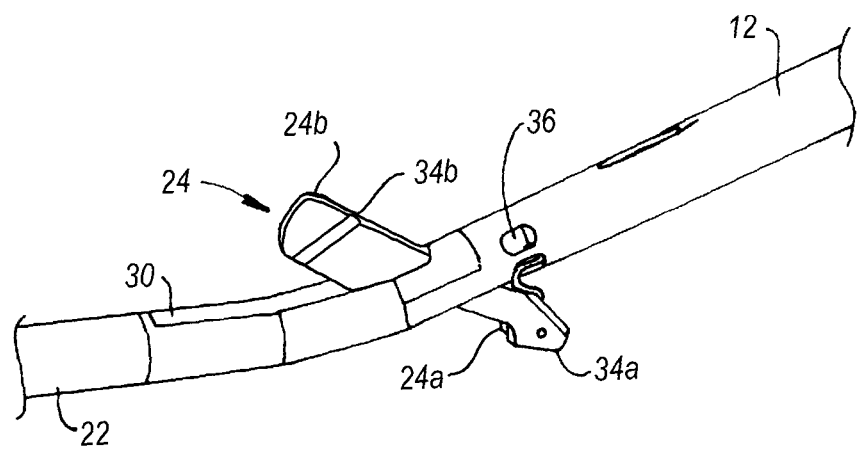
FIG. 4 illustrates the deployment device of FIG. 1 in which an elongate foot is shown in a deployed position in more detail.

Deployment of the foot 24 is illustrated in more detail in FIGS. 3 and 4. In the parked position illustrated in FIG. 3, the foot 24 extends substantially along the axis 28 of the shaft 12. The axis 28 of the shaft 12 need not be straight, as the shaft 12 may curve somewhat, particularly adjacent the foot 24. In the exemplary embodiment, the foot 24 is substantially disposed within a foot receptacle 30 of the shaft 12 so as to minimize the cross-section of the device adjacent the foot 24 prior to deployment. Advantageously, prior to deployment of the foot 24, device 10 can have a cross-section adjacent foot 24 of about 7 Fr or less, ideally having a cross-section of about 6 Fr or less for the entire device distally of the proximal end 14 (FIG. 1) of the shaft 12.

As introduced, actuation of the foot deployment handle 26 (FIGS. 1-2), such as by rotation, deploys the foot 24. In particular, actuation of the foot deployment handle 26 slides a foot actuation wire 32 proximally, pulling foot 24 from a parked position to the deployed position illustrated in FIG. 4. Once deployed, a first end 24a and a second end 24b of foot 24 extend laterally from the shaft. According to the embodiment show, the first end 24a and the second end 24b of the foot 24 include guide channels 34a, 34b defined therein.

The shaft 12 also includes a foot position verification lumen that extends proximally from a position verification port 36 to a position indicator at the proximal housing 18. When the foot 24 is properly positioned within the blood vessel V (FIG. 12), blood pressure will cause blood to flow proximally through the indicator lumen to the indicator. The indicator may optionally include a blood exit port, a clear receptacle in which blood is visible, or the like. In the exemplary embodiment, the indicator can include a length of clear tubing extending from the housing 18 (not shown) in which the blood is clearly visible. It should be understood that a wide variety of alternative position verifications sensors might be used, including electrical pressure sensors, electrolytic fluid detectors, or the like.

Figure 5:
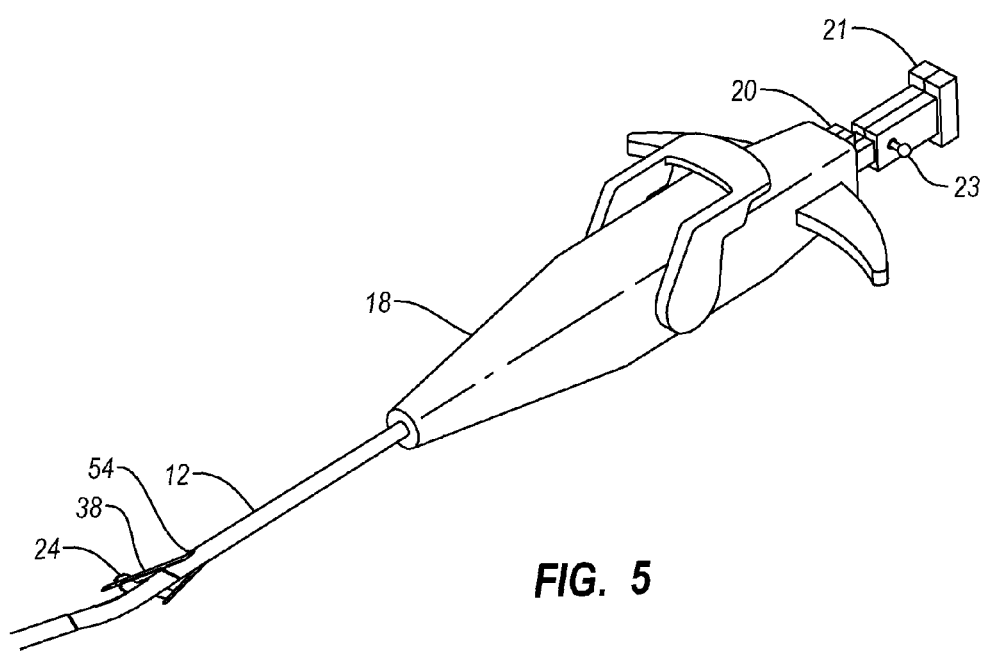

Once the foot 24 has been properly positioned, the needle deployment handle 20 (FIGS. 1-2) may be actuated to deploy a plurality of needles 38 as shown in FIG. 5. As shown in FIG. 5, the needles 38 are advanced outwardly from the shaft 12 and distally toward the foot 24 as the needle deployment handle 20 is urged distally.

FIG. 6 is a partial cutaway view illustrating one of the needles 38 coupled to the needle deployment handle 20. In the present example, the components illustrated may be mirrored such that the deployment of a second hook from a second needle may similarly be described with components similarly designated below. In the illustrated example, the needle 38 can be coupled directly to the needle deployment handle 20. As a result, advancing the needle actuation handle 20 also advances the needle 38.

The needles 38 can be sufficiently stiff to be advanced in compression through the vessel wall (and adjacent tissues) when supported in cantilever. Furthermore, the needles 38 can be flexible enough to be laterally deflected within shaft 12, as can be understood with reference to FIG. 6. The needles 38 may be made of any suitable material. Examples of suitable materials include, without limitation, high strength metals such as stainless steel alloys, polymer, plastics, composites, combinations thereof, or other material having sufficient properties or characteristics to be formed into and/or function as needle 38. In addition, the needles 38 can have any desired length and can be advanced any desired distance. In one configuration, the needles have a length of about 5.0 inches to about 6.0 inches and can be advanced a distance of greater than 0.5 inches. It will be understood, however, that lengths greater and lesser than 5.0 inches are possible, and the advancement of the needles can be greater or lesser than 0.5 inches.

Figures 10, 11:
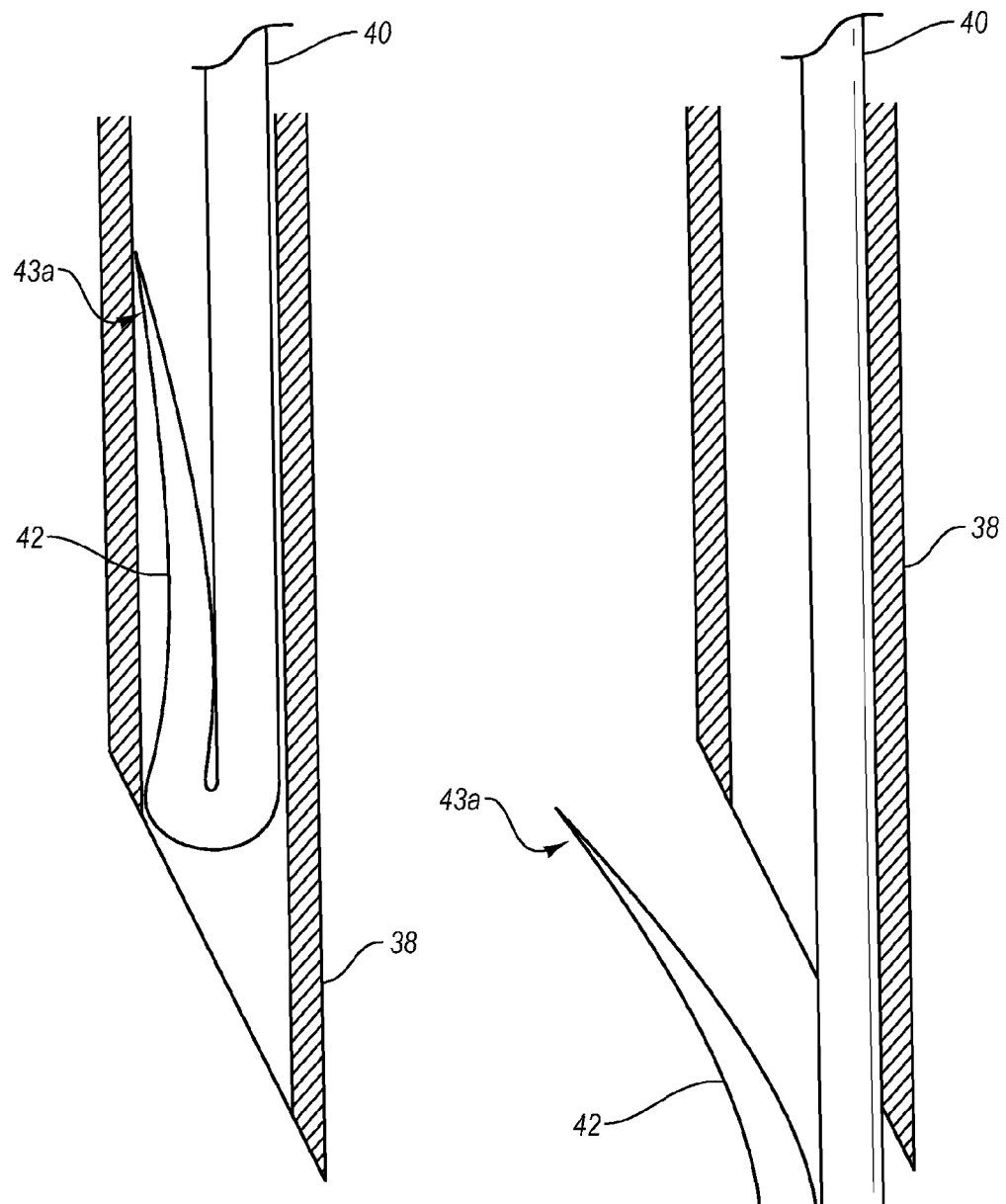
FIG. 10 is a partial cutaway view illustrating a hook located within a needle according to one example.
FIG. 11 is a partial cutaway view illustrating a hook of FIG. 8 outside of a needle according to one example.

FIG. 7 illustrates the needle actuation handle 20 after it has been advanced thereby deploying the needle 38. With the needle deployment handle 20 deployed, the proximal end 41a of the wire 40 can remain at a stationary position within the needle 38. The retention of the proximal end 41a of the wire 40 within the needle 38 may be due, at least in part, to the compression of the hook (not shown) in the distal end 39b of the needle, as shown in FIGS. 10 and 11.

Figure 8:
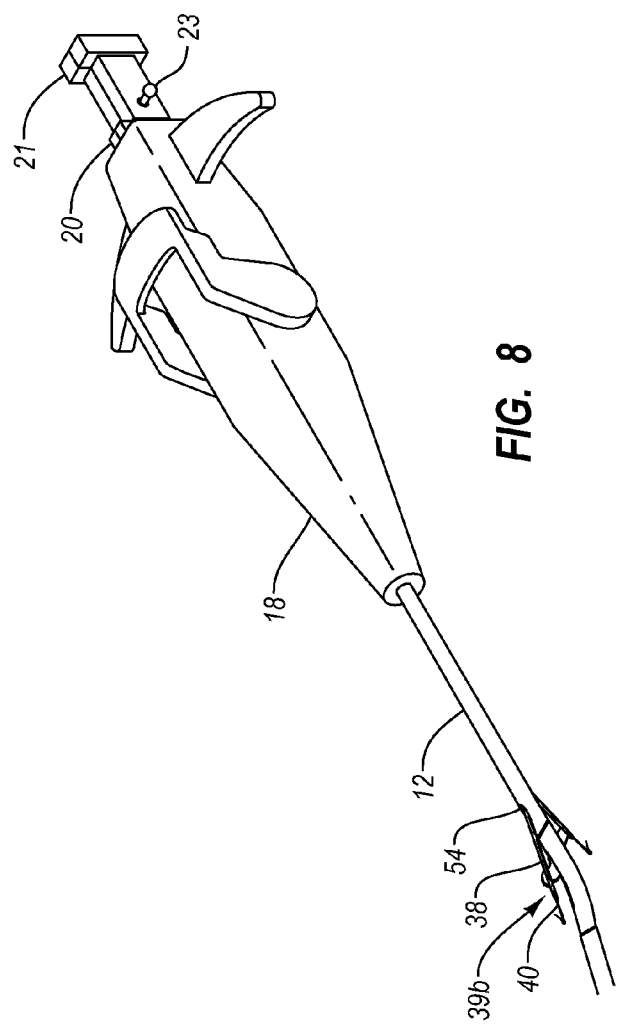
FIGS. 8-9 illustrate deployment of hooks according to one example.
Figure 9:
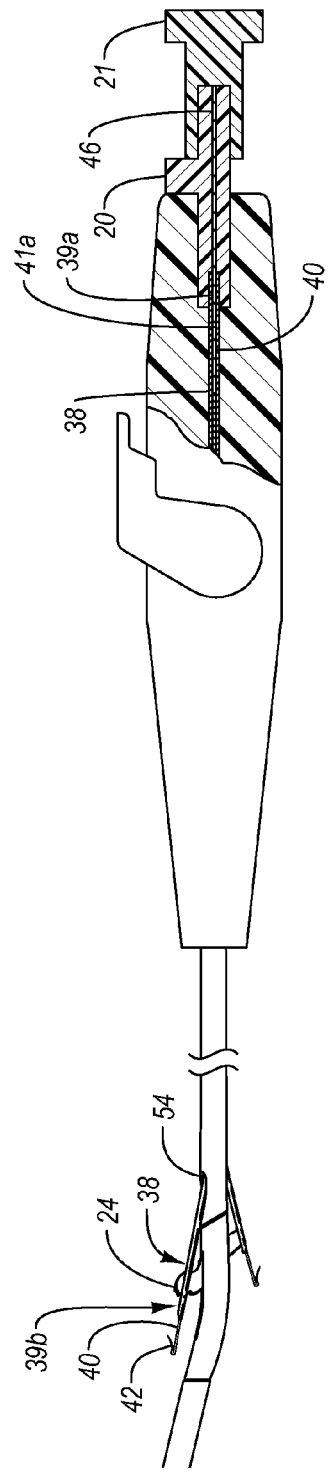

As shown in FIGS. 8 and 9, once the needles 38 have been deployed, the pull pin 23 may be removed and hooks 42 may then be deployed by actuating the hook deployment handle 21 by depressing deployment handle 21. As the hook deployment handle 21 is actuated, the hooks 42 can be advanced outwardly from the distal ends 39b of the needles 38.

More specifically, removing the pull pin 23 allows the hook deployment handle 21 to move relative to the needle deployment handle 20. As illustrated in FIG. 9, a push mandrel 46 can be coupled to the hook deployment handle 21. The push mandrel 46 engages the proximal end 39a of the needle 38. As the push mandrel 46 advances, the push mandrel 46 comes into contact with the proximal end 41a of wire 40 within the proximal end 39a of the needle 38. The push mandrel 46, according to the present example, is a flexible rod of a relatively precise length, although other structure capable of performing the same or similar function can be employed. As the hook deployment handle 21 is advanced relative to the needle deployment handle 20, the push mandrel 46 drives the wire 40 distally, thereby deploying the hooks 42 as illustrated in FIG. 9. The distance between the needle deployment handle 20 and the hook deployment handle 21 as well as the length of the push mandrel 46 are such that fully depressing the deployment handle 21 relative to the needle deployment handle 20 deploys the hooks 42 at a desired location.

In particular, as the hooks 42 are deployed, they are advanced beyond the distal ends 39b of the needles 38 to the desired location as is illustrated in FIG. 9. As the hooks 42 are advanced beyond the distal ends 39b of the needles 38, the hooks 42 decompress from their compressed shape within the needles 38 to their uncompressed or original shape.

FIGS. 10 and 11 illustrate the wires 40 and the interaction between the wires 40 and the needles 38 in more detail. In particular, FIG. 10 is a partial cutaway view illustrating a wire 40 within a needle 38. The distal end of the wire 40 can be doubled over to form the hook 42. As seen in FIG. 10, at least a portion of the wire 40, and in some instances the entire length of the wire 40, including the hook 42, may be located completely within the needle 38 prior to deployment. The wire 40 and the hook 42 according to the present embodiment form a single, unitary member. According to other embodiments, the hook 42 may be formed of one or more materials different from the wire 40. The hook 42 and the wire 40 may then be secured together. Wire 40, the hook 42, and/or any portion of the hook and the wire 40 may be formed of any suitable material, including stainless steel or bioreabsorbable materials, such as magnesium or other such materials.

The hook 42 may also be formed of a resilient material with an original shape. As a result, the hook 42 can be stored in a compressed state entirely within the needle 38. When the wire 40 is extended from the distal end 39b of the needle 38, the hook 42 is freed and returns at least partially to its original shape. As the hook 42 returns toward its original shape, the tip portion 43a moves away from a central axis of the wire 40.

At least a portion of the hook 42 may be flattened and/or sharpened relative to the wire 40 or other more proximal portions of the hook 42. According to the configuration illustrated in FIG. 10, the entire hook 42 is flattened. Flattening the hook 42 allows the hook 42 to fit into a relatively smaller diameter needle. In particular, the diameter of a suitably sized needle can be generally at least as large as the width of the hook 42 when the hook 42 is folded together and compressed as shown in FIG. 10. Flattening at least a portion of the hook 42 decreases the width of the hook 42 when the hook is folded and compressed, thereby allowing the hook 42 to fit in a smaller diameter needle. Flattening at least a portion of the hook 42 may also improve manufacturability. For example, the hook 42 may be rapidly formed using a flattening and folding process. The tips 43a of the hooks 42 can be sharpened. The sharpened tips 43a facilitate anchoring the hooks 42 in a vessel, as will be discussed in more detail below.

Figure 12:
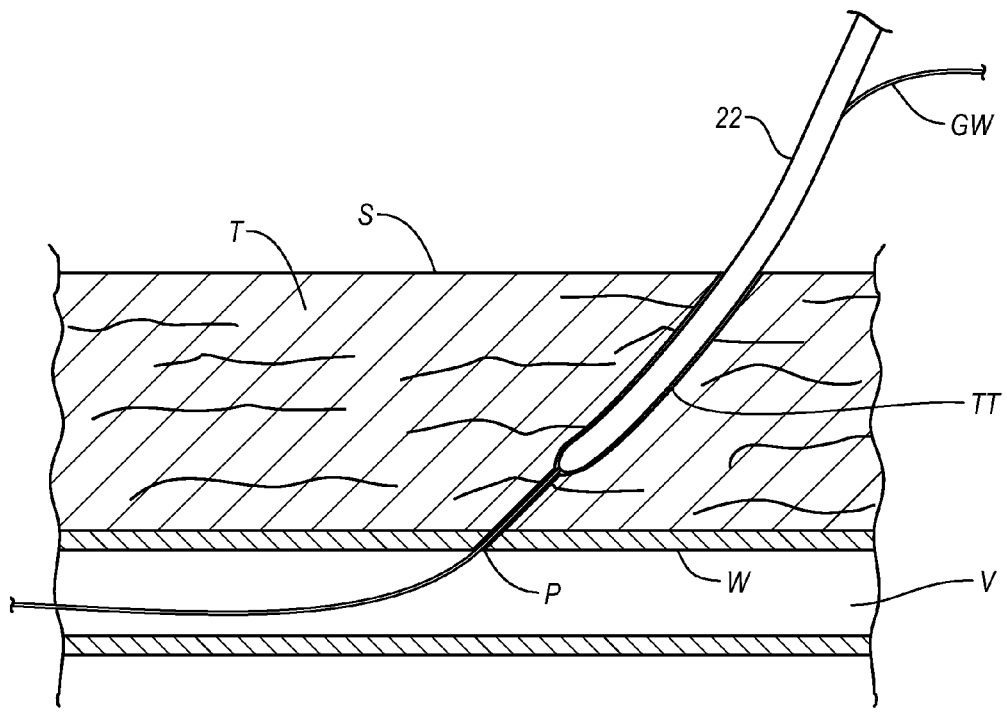
FIG. 12 illustrates a distal end of a shaft of a deployment device being guided over a guidewire in a tissue tract according to one example.

The method of use of the deployment device can be understood with reference to FIGS. 12-15. After accessing a blood vessel V (often using the Seldinger technique), a guidewire GW can extend from the blood vessel V, along tissue tract TT, through tissue T, and extend from skin S. Guidewire GW enters vessel V through a puncture P in the vessel wall W, and extends along the vessel throughout many endovascular procedures. As illustrated in FIG. 12, the distal guidebody 22 can be advanced over the guidewire GW in a monorail fashion, so that the guidewire GW helps to direct the deployment device 10 along the tissue tract TT and into the vessel through puncture P.

Figure 13:
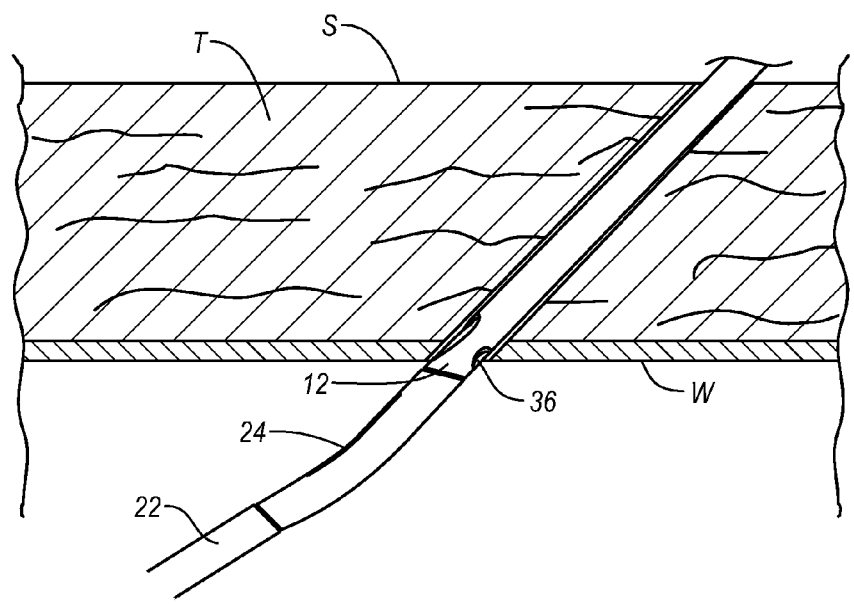
FIG. 13 illustrates a distal end of a shaft of a deployment device initially positioned within a vessel according to one example.

It will be understood that the distal guidebody 22 can be advanced as a rapid-exchange over-the-wire device depending upon the configuration of the device. FIG. 13 shows that when the sensor 36 is disposed within the vessel, blood can flow from the sensor port and through a lumen in shaft 12 to the proximal handle to notify the operator that foot 24 has been advanced far enough for deployment.

Figure 14:
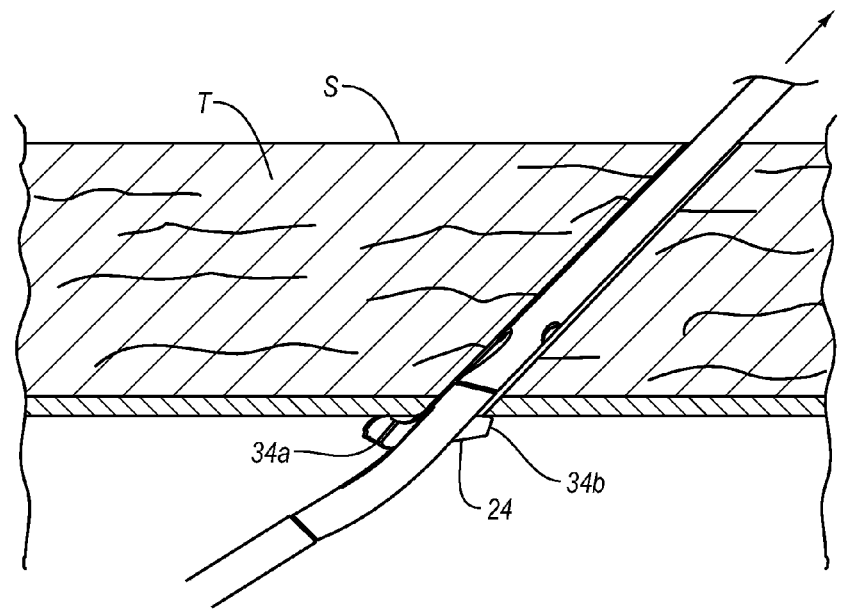
FIG. 14 illustrates an elongate foot deployed and positioned relative to a vessel wall according to one example.

Deployment of the foot 24 can be effected by actuation of the foot deployment handle 26 (FIG. 1), as described and illustrated above. As described above, the guidebody 22 helps to align the shaft 12 with the axis of vessel V. The guidebody 22 may be set at an angle and/or offset relative to shaft 12 as appropriate to aid in alignment with a particular vessel access technique. As shown in FIG. 14, the deployed foot 24 extends laterally from the shaft 12, so that foot 24 adjacent the guide channels 34a, b can be drawn up against vessel wall W by gently pulling shaft 12. Hence, the foot 24 helps to accurately position the needle guides 54 at a distance from the vessel wall W.

Figure 15:
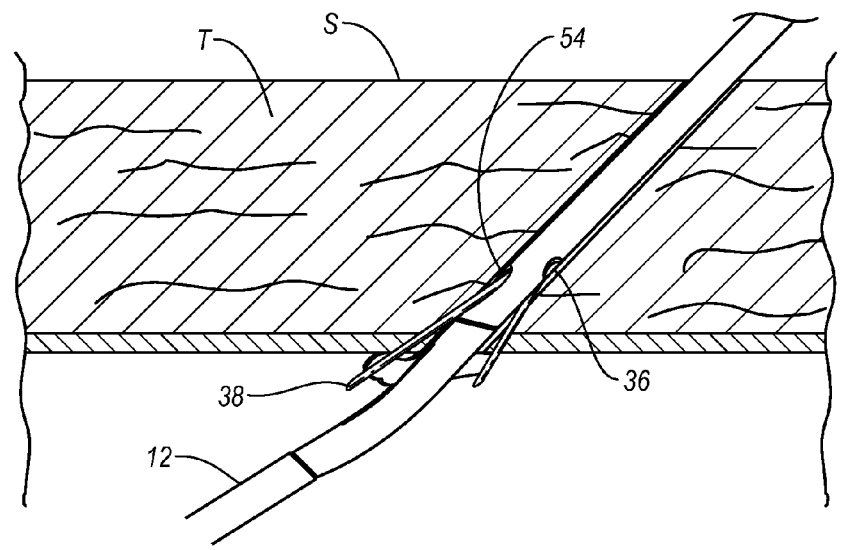
FIG. 15 illustrates needles advancing from a shaft beginning outside a vessel wall and through the vessel wall into a vessel according to one example.

Referring now to FIG. 15, with foot 24 positioned against the vessel wall W, the needles 38 can be advanced in cantilever both distally and laterally when the needle actuation handle 20 is pressed. As the needles 38 advance, the needles 38 are deflected laterally by needle guides 54 toward the guide channels 34a, b of the deployed foot 24. As the needles 38 come into contact with the guide channels 34a, b, the guide channels 34a, b continue to guide the needles 38 as they are advanced in cantilever both distally and laterally from the shaft 12 so as to overcome any unintended deflection of the needles by tissue T or vessel wall W. As a result, the guide channels 34a, b help guide the needles 38 to a desired location within vessel V.

Figure 16:
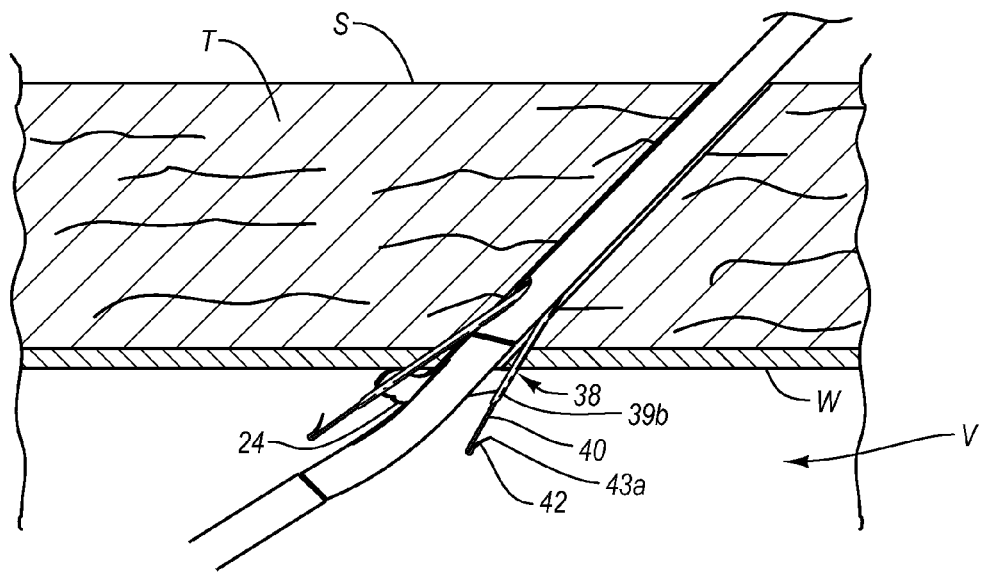
FIG. 16 illustrates needles and hooks deployed within a vessel according to one example.

FIG. 16 illustrates the hooks 42 deployed within the vessel V. When thus deployed, the hooks 42 are located on opposing sides of the puncture P. In this position, the hooks 42 are oriented such that the tips 43a of the hooks 42 point toward the interior of the proximal vessel wall W.

The hooks 42 can then be anchored to the proximal vessel wall W. According to one example, the needles 38 can be anchored by at least partially withdrawing the needles 38 into the guide body 22. In particular, the needle deployment handle 20 may be withdrawn relative to the proximal housing 18. Further, the distal ends 39b of the needles 38 may be completely withdrawn into the guide body 22 such that the distal ends 39b of the needles 38, are withdrawn proximally beyond the needle guides 54 by approximately up to one inch or more.

Figure 17A:
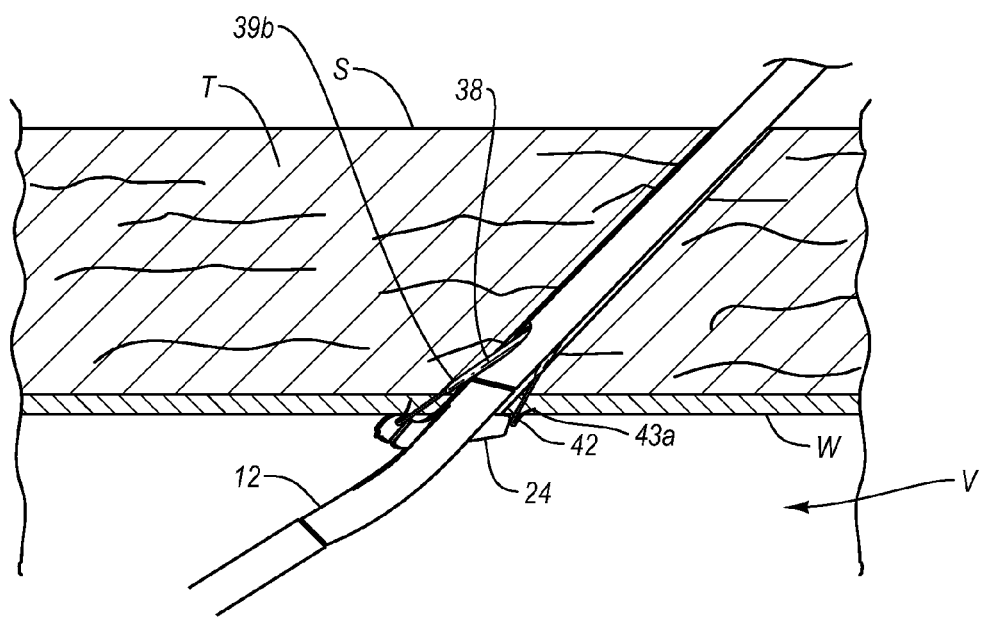
FIG. 17A illustrates a hook anchored to an interior portion of a vessel wall according to one example.

As illustrated in FIG. 17A, when the needles 38 are thus withdrawn, the hooks 42 are drawn into contact with the vessel wall W. In particular, in one example as the needles 38 are withdrawn, the hooks 42 are initially withdrawn as well. As the needles 38 are withdrawn through the vessel wall W, the tips 43a of the hooks 42 are drawn into contact with the vessel wall W. As previously discussed, the tips 43a of the hooks 42 according to the present example are sharpened. Sharpening the tips 43a of the hooks 42 may facilitate the anchoring of the hooks 42 in the vessel wall W.

Once the hooks 42 have been brought into contact with the vessel wall W and the needles 38 have been withdrawn the desired amount, the wires 40 are at least partially freed from the deployment device 10. In particular, according to one example, the hooks 42 are sufficiently anchored to the vessel wall W such that the hooks 42 remain in place as the deployment device 10 is drawn proximally. As the deployment device is drawn proximally, the needles 38, which are located at least partially within the shaft 12, slide over the wires 40, which are anchored to the vessel wall W by the hooks 42. The shaft 12 may be withdrawn until the wires 40 are exposed near the surface of the skin S while portions of the wire remain within the deployment device 10.

Figure 17B:
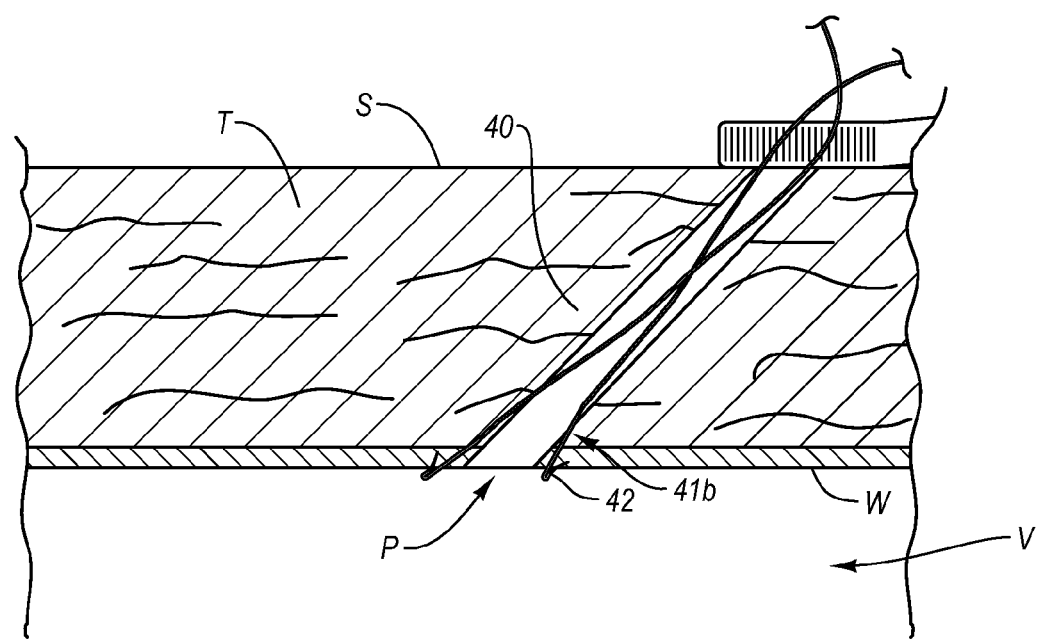
FIG. 17B illustrates a hook anchored to an interior portion of a vessel wall and wires clamped at the surface of the skin according to one example.

After the wires 40 have been exposed from the deployment device 10, the wires 40 may be clamped at the skin surface. The wires 40 may be clamped in any suitable manner. As illustrated in FIG. 17B, the wires 40 may be clamped using surgical clamps and/or another device. According to one example, clamping the wires 40 at the skin surface S maintains tension on the wires 40 between the skin surface S and the vessel wall W. This tension may help ensure the hooks 42 remain anchored to the vessel wall W, and thus remain at or near their deployed location. Accordingly, the deployment device 10 provides for the deployment of wires 40 on opposing sides of the puncture P, such as by anchoring hooks 42 on the distal ends 41b of the wires 40 into the vessel wall W. The wires 40 may then be freed from the deployment device 10.

Figure 18:
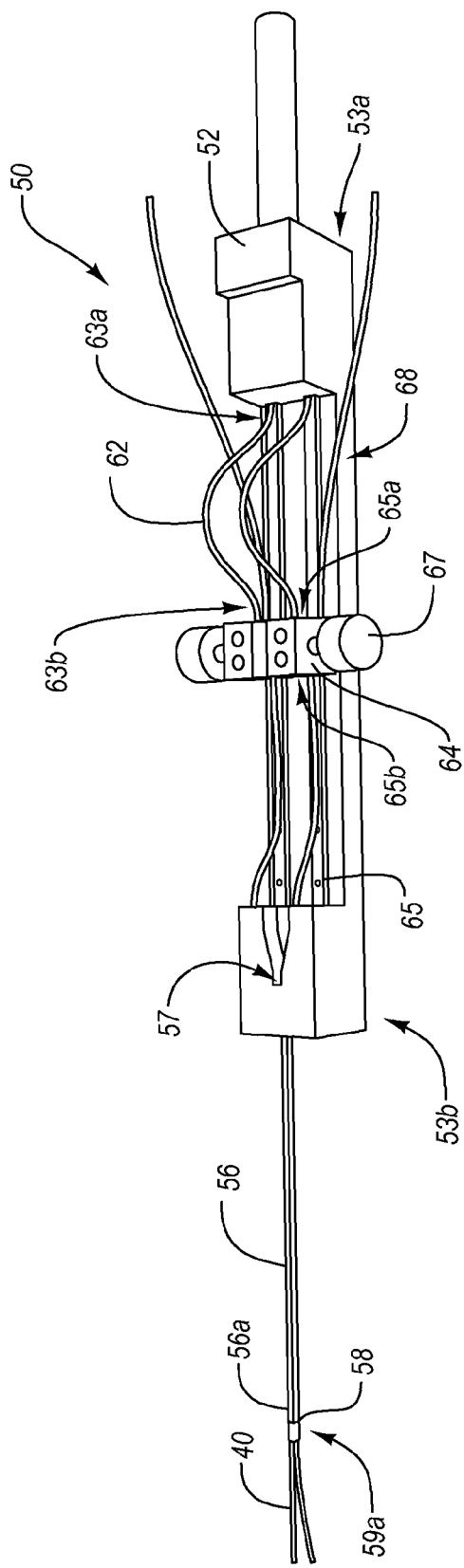
FIG. 18 illustrates a closure device according to one example.

After the wires 40 are clamped at the surface of the skin S, the wires 40 can then be twisted to close the puncture P with the use of a closure device 50 illustrated in FIG. 18. As will be discussed in more detail below, the closure device 50 provides for reliable and repeatable closure of openings in vessel walls. According to one example, the closure device 50 allows a practitioner to twist the wires 40 to secure and close a puncture. Twisting the wires 40 draws opposing sides of the vessel wall together and secures the wires 40 in the relationship, thereby closing the hole. Further, according to the example illustrated in FIG. 18, the closure device 50 provides a substantially constant force on the wires 40 as the wires 40 are twisted, thereby helping ensure that the hooks 42 remain anchored in the vessel wall W. Additionally, according to one example, the closure device 50 initiates the twisting of the wires 40 at a desired location in a repeatable manner.

The closure device 50 generally can include a body 52 with a proximal end 53a and a distal end 53b. Guide lumens 56 extend distally from the distal end 53b of the body 52. A guide tip 58 is coupled to the distal ends 56a of the guide lumens 56. As seen in FIG. 18, the guide tip 58 includes a lumen defined therein that extends through the distal end 59a.

According to the illustrated example, the number or lumens corresponds to the number of wires. Further, the diameter of each of the guide lumens 56 can be selected for use with an associated wire 40. According to one example, the wires 40 can each have substantially the same diameter. The guide lumens 56 of such an example can also have the same diameter. Further, the diameter of the guide lumens 56 may be sufficiently large so that the wires 40 are able to slide freely relative to the guide lumens 56 but sufficiently small to minimize gaps between the guide lumens 56 the wires 40.

As previously introduced, the guide lumens 56 are coupled to the body 52 of the closure device 50. In particular, the body 52 includes a proximal end 53a and a distal end 53b. The guide lumens 56 are in communication with an opening 57 defined in the distal end 53b of the body 52. Biasing members 62, such as constant force springs, can be coupled to the body 52. More specifically, a proximal end 63a of the biasing member 62 can be secured near the proximal end 53a of the body 52.

According to one example, wire securing members 64, such as bosses are coupled to the distal ends 63b of the biasing members 62. The wire securing members 64 can be, in turn, coupled to linear slides 65 that are secured to the body 52. The wire securing members 64 are configured to slide relative to the linear slides 65 in response to movement of the biasing members 62. The wire securing members 64 are configured to secure wires 40 to the biasing members 62. More specifically, each of the wire securing members 64 can include a lumen (not shown) defined therein that passes from the distal end 65b to the proximal end 65a, thereby allowing a wire 40 to pass therethrough.

The wire securing members 64 can further include clamping members 67, such as setscrews. According to the present example, wires 40 are passed through the wire securing members 64 and secured to the wire securing members 64 by the clamping members 67. Those of skill in the art will appreciate that other configurations are possible, such as a lumen that does not extend completely through the boss or that passes through some other location other than the distal or proximal end. Further, those of skill in the art will appreciate that other types of clamping members may be used to secure wires to the wire securing members 64, such as clamps, clips, or other types of clamping, securing or retaining devices. In any case, clamping or securing members, such as the clamping members 67, secure wires 40 to the wire securing members 64 and thus couple the wires 40 to the biasing members 62.

As introduced, the wires 40 can pass through the guide tip 58 through the distal end 53b of the body 52 and through the wire securing members 64. Thereafter, the wires 40 can be secured with the clamping members 67. According to one example, the linear slides 65 are located within a recess 68 formed in the body 52. In particular, the recess 68 is such that relatively smooth pathways are defined through the guide lumens 56, the opening 57 in the distal end 53b of the body 52, and through the wire securing members 64. In such a configuration, the linear slides 65 help ensure the tensioning force exerted on the wires 40 act parallel to each other, thereby helping ensure the twists will be more uniform.

Figure 19:
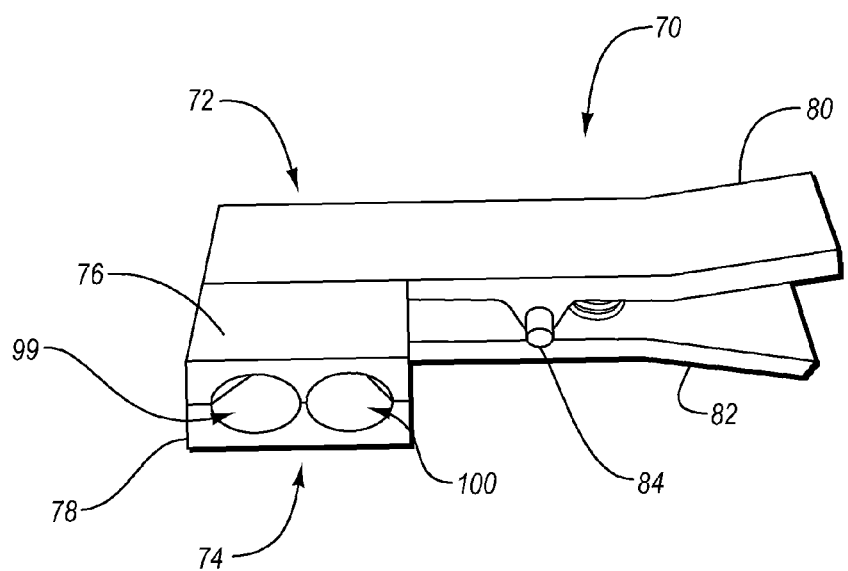
FIG. 19 illustrates a loading device according to one example.

FIG. 19 illustrates a wire-loading device 70 that facilitates the introduction or loading of the wires 40 into the corresponding guide lumens 56 (FIG. 18) of the closure device 50 (FIG. 18). In particular, as illustrated in FIG. 19, the wire-loader 70 can include opposing sides 72, 74. The opposing sides 72, 74 each include body portions 76, 78 and handle portions 80, 82. For ease of reference, a closed configuration will be described in which the body portions 76, 78 are relatively close to one another, such as in contact with one another while an open configuration will be described in which the body portions 76, 78 are separated by a greater distance than in a closed configuration.

Figure 20:
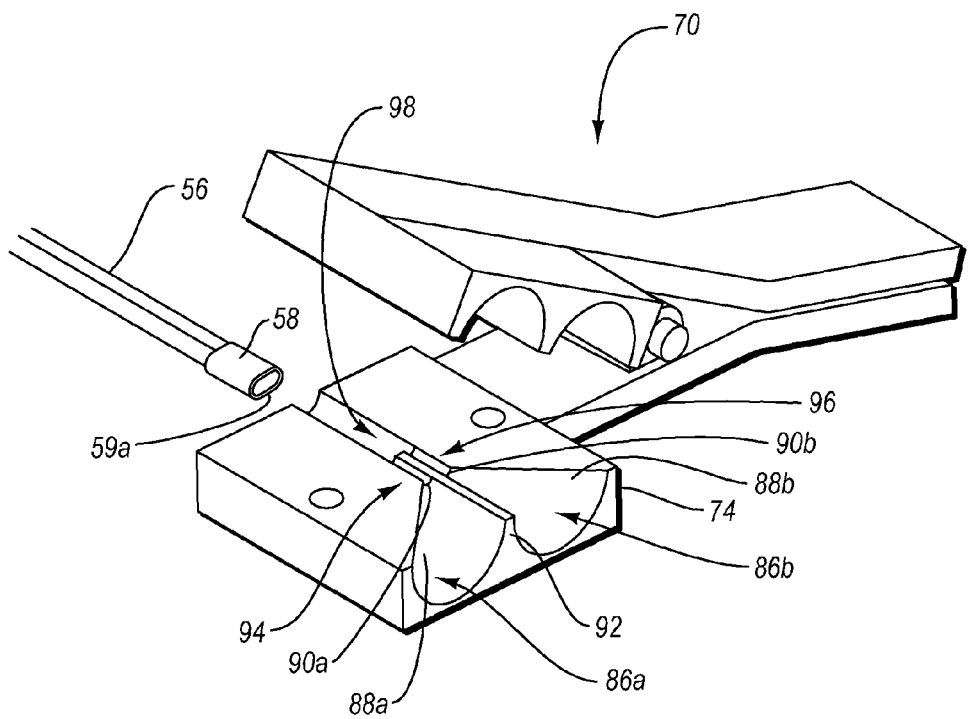
FIG. 20 illustrates the loading device of FIG. 19 in an open configuration according to one example.

The opposing sides 72, 74 are coupled together with a pin 84. The pin 84 allows the opposing sides 72, 74 to pivot relative to each other between the closed and open positions shown in FIGS. 19 and 20 respectively. The opposing sides 72, 74 have recesses 86a, b defined therein. As illustrated in FIG. 20, the recesses 86a, b defined in the second side 74 will be discussed. Those of ordinary skill in the art will appreciate that corresponding recesses may be defined in the first opposing side 72. The recesses 86a, b include oblique semi-conical portions 88a, b. The oblique semi-conical portions 88a, b taper toward the center of the second side 74 to apexes 90a, b. A ridge 92 separates each of the oblique semi-conical portions 88a, b. The ridge 92 further extends beyond the apexes 90a, b to form intermediate lumens 94, 96.

The intermediate lumens 94, 96 are in turn in communication with a tip engaging feature 98. When the first and second sides 72, 74 are brought into contact with each other, the recesses 86a, b form complete features, including the tip engaging feature 98. The tip engaging feature 98 is sized to receive the guide tip 58 of the closure device 50. The other features of the wire-loading device 70 cooperate to aid in loading or introducing wires 40 to the closure device 50, as will now be discussed in more detail.

As previously introduced, during a vessel closure procedure, the wires 40 are freed from the deployment device 10 (FIG. 1). Once the wires 40 are freed, the wire-loading device 70 may be used to introduce the wires 40 into the closure device 50. For example, the closure device 50 may be coupled to the wire-loading device 70 by placing a distal portion 59a of the guide tip 58 into the tip engaging feature 98 within the wire-loading device 70. The features of the wire-loading device 70 are configured so that when the guide tip 58 is thus coupled to the tip engaging feature 92, the axes of the intermediate lumens 94, 96 (FIG. 19) of the wire-loading device 70 and the guide lumens 56 are aligned. Such a configuration facilitates the loading of the wires 40. For example, the oblique semi-conical portions 88a, b cooperate to form funneled openings 99, 100, which are illustrated in FIG. 19. The funneled openings 99, 100 are relatively large as compared to the intermediate lumens 94, 96. The funneled openings 99, 100 lead to the apexes 90a, b (FIG. 20) and then to the intermediate lumens 94, 96 such that when a user feeds the wires 40 proximally into the funnel openings 99, 100, the funneled openings 99, 100 and the ridge 98 guide the ends of the wires 40 into the intermediate lumens 94, 96.

Thereafter, the intermediate lumens 94, 96 guide the wires into the guide lumens 56. In particular, the intermediate lumens 94, 96 and the guide lumens 56 are sufficiently aligned that when the ends of the wires 40 (not shown) are introduced through the funneled openings 99, 100, the ends of the wires 40 pass through the intermediate lumens 94, 96, through the guide tip 58, and into the distal ends 59a of the guide lumens 56. Thereafter, the wires 40 may be fed though the distal end 53b of the body 52 and thence through the wire securing members 64.

Figure 21:
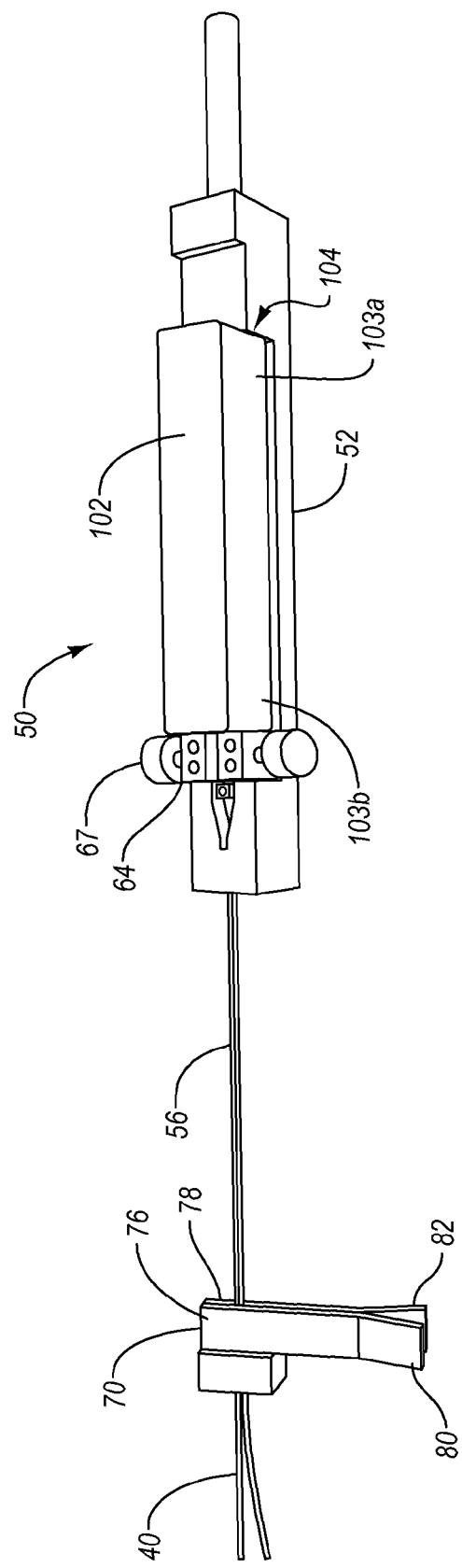
FIG. 21 illustrates a loading device and a preloading block coupled to a closure device according to one example.

FIG. 21 illustrates the wire-loading device 70 coupled to the guide tip 58 as previously discussed. After the wires 40 have been fed into the guide lumens 56, the wire-loading device 70 may be removed. In particular, according to one example, the wire-loading device 70 may be opened by pressing the handle portions 80, 82 together to separate the body portions 76, 78, thereby allowing the wire-loading device 70 to be withdrawn from the wires 42.

It may be desirable to retain the biasing members 62 in a preloaded or preliminarily deflected position. While undeflected, the biasing members 62 (FIG. 18) extend from the proximal end 53b toward the distal end 53a of the body 52. The biasing members 62 are preloaded by moving the biasing members 62 toward the distal end 53b of the body 52. FIG. 21 also illustrates a preloading block 102 coupled to the body 52. In particular, a distal end 103b of the preloading block 102 is in contact with the wire securing members 64 while the proximal end 103a is in position at a shoulder 104 formed by the recess 68 (FIG. 18) in the distal end 53a of the body 52. Thus positioned, the preloading block 102 retains each biasing members 62 in a preloaded position. While a preloading block 102 is shown, those of skill in the art will appreciate that other types of preloading devices may be used to retain biasing members such as the biasing members 62 in a preloaded position. Suitable retention devices may include, without limitation, latches, hooks, clips, or any other devices or structures suitable for retaining biasing members in a preloaded position.

According to one example, the wires 40 are secured to the wire securing members 64 while the preloading block 102 is in place. For example, as previously discussed, the wire securing members 64 may have channels or lumens that extend therethrough. The free ends of the wires 40 may be fed through the wire securing members 64 and the closure device 50 advanced proximally over the wires 40 until the guide tip 58 is relatively near the vessel wall W, such as near the surface of the skin. Thereafter the clamping members 67 may be tightened to thereby secure the wires 40 to the bosses 64.

The preloading block 102 can then removed, thereby causing the biasing members 62 to draw the wire securing members 64 and the wires 40 proximally along the linear slides 65. As previously discussed, the hooks 42 are anchored to the vessel wall W (best illustrated in FIG. 17A). As a result, as the wire securing members 64 and wires 40 are drawn proximally, the guide tip 58 is drawn distally and thus toward the vessel wall W. It may be desirable to place the distal end of the guide tip 58 in contact with the proximal surface of the vessel wall W.

After the guide tip 58 has been placed into contact with the vessel wall W, the entire closure device 50 is rotated to twist the wires 40 relative to each other. As previously discussed, several features may be implemented that facilitate reliable and repeatable twisting of the wires 40 in such a manner as to achieve closure of the puncture and hemostasis.

For example, placing the guide tip 58 in contact with the vessel wall W provides an established gap between the vessel wall W and the guide lumens 56. Providing such an established gap provides for a reliable point away from the vessel wall W for the twist to begin. In particular, the guide tip 58 is sized such that when the entire closure device 50 is rotated to twist the wires 40, the twist in the wires is initiated within the guide tip 58. Beginning the twist at a location away from the vessel wall prevents trauma to the vessel tissue that may be associated with initiating the twist directly on the vessel wall, where pinching or distortion of the normal vessel shape might occur.

The reliability of the closure device may be enhanced by providing selectively annealed wires 40. In particular, the portion of the wires 40 wherein twisting is desired to occur may be spot annealed. Spot annealing softens metal. Thus, spot annealing the portion of the wires where twisting is desired may facilitate twisting of the wires in that portion. Additionally, twists formed of stiffer materials may unwind as the wires may be more difficult to sufficiently deform in a fully plastic manner. As a result, twists of stiffer material may tend to return to their untwisted shapes, thereby causing the twist to unwind. Consequently, wires having spot annealed portions may be twisted in a manner in which the twist is less likely to unwind. According to one example, the spot annealed section of each wire may be approximately one centimeter in length.

Further, it may be desirable to apply a substantially constant and equal force to each of the wires 40 to the guide tip 58 as the guide tip 58 is in contact with the proximal surface of the vessel wall W. In particular, applying a substantially constant and equal force to each of the wires 40 may provide for consistent twisting of the wires relative to each other and relative to the vessel wall W while reducing the possibility that the wires 40 will pull through the vessel wall W.

Each of the biasing members 62 of the present example slide independently along the associated linear slides 65 in response to the forces independently applied by each of the biasing members 62. As a result, each wire 40 is tensioned independently. Further, the biasing members 62 apply relatively constant tension to each of the wires 40 throughout their range of displacement. Thus, the biasing members 62 apply a relatively constant force to the wires 40 while the guide tip 58 is in contact with the vessel wall W. The linear slide 65 helps ensure the forces applied to each wire 40 by the biasing members 62 are parallel to a central axis of the closure device 50. This in turn may facilitate even twisting of the wires 40. Additionally, maintaining a relatively constant force on the wires 40 may help ensure that the hooks 42 will remain anchored in the vessel wall W (FIG. 17A).

Figure 22:
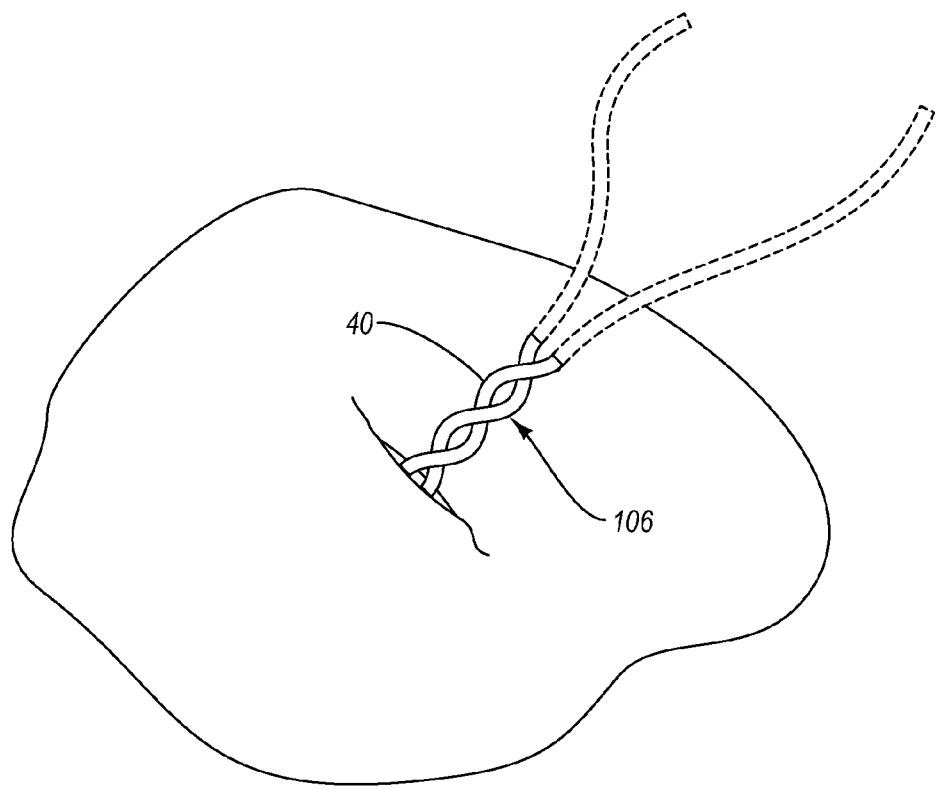
FIG. 22 illustrates twists in a wire according to one example.

FIG. 22 illustrates the wires 40 twisted and the closure device 50 (FIG. 18) has been withdrawn. The twists 106 secure the closure to establish hemostasis. After the wires 40 have been twisted and the closure device 50 removed, a portion of the wires 40 above the twist 106 may be clipped or otherwise removed, as indicated by the dashed lines. Another design embodiment could be a predetermined break-off location on each wire. Break off locations can be created with a crimp or narrowing of the wires where the wires will separate when the twisting torque reaches a certain threshold.

FIG. 23 illustrates another example of a wire 40 located within a needle 38. In particular, FIG. 23 is a partial cutaway view illustrating a wire 40 within a needle 38. The distal end of the wire 40 forms a generally T-shaped hook 42'. The T-shaped hook 42' includes a proximal tip portion 44a and a distal tip portion 45a. As seen in FIG. 23, at least part of the proximal tip portion 44a, and in some instances the entire length of the wire 40, including the proximal tip portion 44a and the distal tip portion 45a, may be located completely within the needle 38 prior to deployment.

In such a configuration, the proximal and distal tip portions 44a, 45a may be aligned relative to wire 40 in such a manner that the wire 40 and the proximal and/or distal tips 44a, 45a may parallel with an extended central axis of the wire 40 or may be positioned at angles relative an extended axis of the wire 40. The proximal and distal tip portions 44a, 45a may be positioned in any manner. For example, the proximal and distal tip portion 44a, 45a may be co-linear, the proximal and distal portions 44a, 45a may be at similar angles relative to an extended central axis of the wire 40 or may be at different angles relative to an extended central axis of the wires 40.

The wire 40 and the hook 42' according to at least one example form a single, unitary member. According to other embodiments, the hook 42' may be formed of one or more materials different from the wire 40. The hook 42' and the wire 40 may then be secured together. Wire 40, the hook 42', and/or any portion of the hook and the wire 40 may be formed of any suitable material, including stainless steel or bio-reabsorbable materials, such as magnesium or other such materials.

The hook 42' may also be formed of a resilient material with an original shape. As a result, the hook 42' can be stored in a compressed state within the needle 38. When the wire 40 is extended from the distal end 39a of the needle 38, the hook 42' is freed and returns at least partially to its original uncompressed shape.

FIG. 24 illustrates the hook 42' returning generally to its uncompressed shape. As the hook 42' transitions toward the uncompressed shape, the hooks 42' may move from a position in which the proximal and distal tip portions 44a, 45a move away from their stored positions. In particular, as the hook 42' returns toward the uncompressed shape, the proximal and distal tip portions 44a, 45a move from alignment with an extended central axis of the wire 40 to provide and/or increase angular separation between the extended central axis of the wire 40. In at least one example, this separation moves the hook 42' to the deployed T-shape illustrated in FIG. 24.

In the deployed position, the proximal and distal tip portions 44a, 45a extend away from the wire 40. When located within a body lumen as described above, the extension of the proximal and distal tip portions 44a, 45a allows the hook 42' to engage a vessel wall W (FIG. 17B). Accordingly, the hook 42' may be deployed to provided engagement for the wire 40.

Optionally, the proximal tip portion 44a and/or the distal tip portion 45a can included one or more securing structures or features, such as barbs 47, that can engage the tissue and aid with securing the hook 42' with the vessel wall W (FIG. 17B). These securing structures or features can have various configurations so long as they aid with securing the hook 42' to the vessel wall W (FIG. 17B).

In conclusion, a closure system is provided herein that includes a deployment device and a closure device. The deployment device provides for repeatable and reliable deployment of wires within a vessel having a puncture therein while the closure device provides reliable and repeatable closure of the puncture with the wires.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for deploying a suture in a puncture through a vessel wall of a blood vessel, the puncture disposed within a tissue tract of a patient body, the device comprising:
    a shaft suitable for insertion along the tissue tract and into the vessel through a puncture;
    a foot coupled to the shaft, the foot including a plurality of guide channels extending through the foot from a proximal side to a distal side of the foot;
    a plurality of hollow needles, each needle having a proximal end, a distal end suitable for forming a needle path through the vessel wall, each needle configured to extend from the proximal side of the foot, through a respective guide channel of the plurality of guide channels, and distally beyond the distal side of the foot;
    wires associated with each needle, each wire being slidably disposed within a hollow needle of the plurality of needles and having a distal end and a proximal end; and
    hooks coupled to each of the distal ends of each wire, each hook being configured to anchor the wire to an interior portion of the vessel wall, the slidable movement of the wires and deployment of the hooks from within the plurality of hollow needles being independent from proximal movement of the needle.

2. The device of claim 1, wherein at least one hook is configured to be stored completely within one of the needles prior to deployment and to be extended beyond the distal end of the needle after deployment.

3. The device of claim 1, wherein the foot is configured to move from a low profile configuration aligned along the shaft to a deployed configuration extending laterally from the shaft and along the vessel and wherein the first and second needles are advanced from a stored positioned within the shaft through the vessel wall outside the puncture.

4. The device of claim 3, wherein the guide channels defined therein are configured for guiding the needles as the needles advance in cantilever and distally relative to the shaft.

5. The device of claim 1, further comprising a proximal body and a needle deployment handle coupled to the proximal end of the needles, wherein moving the needle deployment handle toward the proximal body deploys the needles.

6. The device of claim 5, further comprising a hook deployment handle, wherein moving the hook deployment handle distally relative to the needle deployment handle deploys the hooks.

7. The device of claim 6, further comprising a pull pin configured to retain the hook deployment handle in position relative to the needle deployment handle as the needle deployment handle is moved toward the proximal body to deploy the needles and is configured to be removed to allow the hook deployment handle to move distally relative to the needle deployment handle to deploy the hooks.

8. The device of claim 6, wherein the hook deployment handle has a push mandrel coupled thereto, the push mandrel being configured to deploy the hooks when the hook deployment handle is moved distally relative to the needle deployment handle.

9. The device of claim 1, wherein at least one of the hooks comprises a single tip configured to move away from at least one of the wires.

10. The device of claim 1, wherein at least one of the hooks comprises a plurality of tips configured to form a T-shape when deployed.

11. A device for deploying a suture in a puncture through a vessel wall of a blood vessel, the puncture disposed within a tissue tract of a patient body, the device comprising:
a shaft suitable for insertion along the tissue tract and into the vessel through a puncture;
a foot coupled to the shaft, the foot including a plurality of guide channels extending through the foot from a proximal side to a distal side of the foot;
a plurality of hollow needles, each needle having a proximal end, a distal end suitable for forming a needle path through the vessel wall, and a needle deployment handle disposed at the proximal end of each needle, each needle configured to extend from the proximal side of the foot, through a respective guide channel of the plurality of guide channels, and distally beyond the distal side of the foot;
wires associated with each needle, each wire having a distal end and a proximal end and being disposed within a hollow needle of the plurality of hollow needles; and
hooks coupled to each of the distal ends of each wire, each hook being configured to anchor the wire to an interior portion of the vessel wall and having a proximally extending portion that initially extends towards the wire and subsequently extends outwardly away from the wire, each wire including a hook deployment handle disposed at the proximal end of the wire, the hook deployment handle slidably cooperating with a proximal end of the needle deployment handle.

12. The device of claim 11, wherein at least one hook is configured to be stored completely within one of the needles prior to deployment and to be extended beyond the distal end of the needle after deployment.

13. The device of claim 11, wherein the hooks further comprise a sharpened tip.

14. The device of claim 11, wherein a portion of the hooks is flattened.

15. The device of claim 11, wherein the wire comprises a break-off location to separate the wire into two portions.

16. The device of claim 15, further comprising a hook deployment handle.

17. The device of claim 11, wherein the foot is configured to move from a low profile configuration aligned along the shaft to a deployed configuration extending laterally from the shaft and along the vessel.

18. The device of claim 11, further comprising a proximal body and a needle deployment handle coupled to the proximal end of the needles.

* * * * *